United States Patent
Brannan

(10) Patent No.: US 8,394,092 B2
(45) Date of Patent: Mar. 12, 2013

(54) ELECTROMAGNETIC ENERGY DELIVERY DEVICES INCLUDING AN ENERGY APPLICATOR ARRAY AND ELECTROSURGICAL SYSTEMS INCLUDING SAME

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 606 days.

(21) Appl. No.: 12/620,289

(22) Filed: Nov. 17, 2009

(65) Prior Publication Data
US 2011/0118721 A1 May 19, 2011

(51) Int. Cl.
*A61B 18/18* (2006.01)
(52) U.S. Cl. .......................... 606/41; 606/34
(58) Field of Classification Search ............ 606/34, 606/41
See application file for complete search history.

(56) References Cited

U.S. PATENT DOCUMENTS

| | | | |
|---|---|---|---|
| 4,397,313 A | 8/1983 | Vaguine | |
| 4,700,716 A | 10/1987 | Kasevich et al. | |
| 4,741,348 A | 5/1988 | Kikuchi et al. | |
| 4,798,215 A | 1/1989 | Turner | |
| 4,815,479 A | 3/1989 | Carr | |
| 4,860,752 A | 8/1989 | Turner | |
| 4,974,587 A * | 12/1990 | Turner et al. | 607/101 |
| 5,057,106 A | 10/1991 | Kasevich et al. | |
| 5,097,844 A | 3/1992 | Turner | |
| 5,220,927 A * | 6/1993 | Astrahan et al. | 607/156 |
| 5,251,645 A * | 10/1993 | Fenn | 607/154 |
| 6,016,452 A | 1/2000 | Kasevich | |
| 6,347,251 B1 | 2/2002 | Deng | |
| 6,398,781 B1 | 6/2002 | Goble et al. | |
| 6,582,427 B1 | 6/2003 | Goble et al. | |
| 7,565,207 B2 | 7/2009 | Turner et al. | |
| 2002/0022836 A1 | 2/2002 | Goble et al. | |
| 2004/0044385 A1 * | 3/2004 | Fenn et al. | 607/100 |
| 2007/0255269 A1 * | 11/2007 | Shin | 606/34 |
| 2008/0281314 A1 * | 11/2008 | Johnson et al. | 606/34 |
| 2009/0326620 A1 | 12/2009 | Rossetto et al. | |
| 2010/0030206 A1 * | 2/2010 | Brannan et al. | 606/33 |
| 2010/0053015 A1 * | 3/2010 | Willyard | 343/790 |
| 2010/0057070 A1 * | 3/2010 | Behnke et al. | 606/33 |
| 2010/0076422 A1 * | 3/2010 | Podhajsky | 606/32 |
| 2010/0082082 A1 * | 4/2010 | Prakash et al. | 607/101 |
| 2010/0087808 A1 * | 4/2010 | Paulus | 606/33 |

(Continued)

FOREIGN PATENT DOCUMENTS

DE 390937 3/1924
DE 1099658 2/1961

(Continued)

OTHER PUBLICATIONS

U.S. Appl. No. 08/483,742, filed Jun. 7, 1995, Stern et al.*

(Continued)

*Primary Examiner* — Linda Dvorak
*Assistant Examiner* — Jocelyn D Ram

(57) ABSTRACT

An electrosurgical system for directing energy to tissue includes a generator assembly operable to supply power having a selected phase, amplitude and frequency, and an applicator array assembly. The applicator array assembly includes a shell assembly, a plurality of energy applicators disposed within the shell assembly, and a power divider unit electrically coupled to the generator assembly. The power divider unit is operable to divide power into the applicator array assembly.

11 Claims, 12 Drawing Sheets

U.S. PATENT DOCUMENTS

| | | | |
|---|---|---|---|
| 2010/0092939 A1* | 4/2010 | Belous et al. | 435/1.2 |
| 2010/0094272 A1* | 4/2010 | Rossetto et al. | 606/33 |
| 2010/0094273 A1* | 4/2010 | Rossetto et al. | 606/33 |
| 2010/0097284 A1* | 4/2010 | Brannan et al. | 343/793 |
| 2010/0217251 A1* | 8/2010 | Rossetto et al. | 606/33 |
| 2010/0217252 A1* | 8/2010 | Rossetto et al. | 606/33 |
| 2010/0234839 A1* | 9/2010 | Smith et al. | 606/33 |
| 2010/0250209 A1* | 9/2010 | Pearson et al. | 703/2 |
| 2010/0256624 A1* | 10/2010 | Brannan et al. | 606/33 |
| 2010/0262134 A1* | 10/2010 | Jensen et al. | 606/33 |
| 2010/0286681 A1* | 11/2010 | Podhajsky | 606/33 |
| 2010/0286682 A1* | 11/2010 | Podhajsky | 606/33 |
| 2010/0286683 A1* | 11/2010 | Podhajsky | 606/33 |
| 2010/0305559 A1* | 12/2010 | Brannan et al. | 606/33 |
| 2010/0305560 A1* | 12/2010 | Peterson | 606/33 |
| 2010/0305561 A1* | 12/2010 | Prakash et al. | 606/33 |
| 2010/0321192 A1* | 12/2010 | Brannan | 340/600 |
| 2010/0321257 A1* | 12/2010 | Brannan | 343/703 |
| 2010/0331834 A1* | 12/2010 | Peterson et al. | 606/41 |
| 2011/0012679 A1* | 1/2011 | Behnke | 330/269 |
| 2011/0034913 A1* | 2/2011 | Brannan | 606/33 |
| 2011/0034917 A1* | 2/2011 | Brannan | 606/33 |
| 2011/0034919 A1* | 2/2011 | DeCarlo | 606/41 |
| 2011/0040300 A1* | 2/2011 | Brannan | 606/41 |
| 2011/0054458 A1* | 3/2011 | Behnke | 606/33 |
| 2011/0054459 A1* | 3/2011 | Peterson | 606/33 |
| 2011/0060325 A1* | 3/2011 | Bonn | 606/33 |
| 2011/0060326 A1* | 3/2011 | Smith et al. | 606/33 |
| 2011/0066144 A1* | 3/2011 | Bonn et al. | 606/33 |
| 2011/0071511 A1* | 3/2011 | Brannan et al. | 606/33 |
| 2011/0071512 A1* | 3/2011 | Behnke et al. | 606/33 |
| 2011/0071582 A1* | 3/2011 | Willyard et al. | 607/2 |
| 2011/0073594 A1* | 3/2011 | Bonn | 219/759 |
| 2011/0077632 A1* | 3/2011 | Rossetto | 606/33 |
| 2011/0077633 A1* | 3/2011 | Bonn et al. | 606/33 |
| 2011/0077634 A1* | 3/2011 | Brannan | 606/33 |
| 2011/0077635 A1* | 3/2011 | Bonn | 606/33 |
| 2011/0077636 A1* | 3/2011 | Brannan et al. | 606/33 |
| 2011/0077637 A1* | 3/2011 | Brannan | 606/33 |
| 2011/0077638 A1* | 3/2011 | Brannan | 606/33 |
| 2011/0077639 A1* | 3/2011 | Brannan et al. | 606/33 |
| 2011/0092972 A1* | 4/2011 | Allen | 606/45 |
| 2011/0098695 A1* | 4/2011 | Brannan | 606/33 |
| 2011/0098696 A1* | 4/2011 | Brannan | 606/33 |
| 2011/0098697 A1* | 4/2011 | Brannan | 606/33 |
| 2011/0118721 A1* | 5/2011 | Brannan | 606/33 |
| 2011/0118731 A1* | 5/2011 | Ladtkow | 606/41 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | 2008/012827 A2 | 1/2008 |
| WO | 2009/128940 A1 | 10/2009 |

OTHER PUBLICATIONS

U.S. Appl. No. 08/136,098, filed Oct. 14, 1993, Stern et al.*
European Search Report for European Application No. EP10014705 dated Apr. 28, 2011.
European Search Report for European Application No. 10014705 dated Apr. 27, 2011.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OGB Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 941n Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., Theoretical Aspects of "Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman et al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•Linear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Intl Federation of Gynecology and Obstetrics Figo World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L. W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High FrequencY Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.

European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

ELECTROMAGNETIC ENERGY DELIVERY DEVICES INCLUDING AN ENERGY APPLICATOR ARRAY AND ELECTROSURGICAL SYSTEMS INCLUDING SAME

BACKGROUND

1. Technical Field

The present disclosure relates to electrosurgical devices suitable for use in surface ablation applications and, more particularly, to electromagnetic energy delivery devices including an energy applicator array and electrosurgical systems including the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a long, thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna. The design of the microwave applicator radiating antenna(s) influences the thermal distribution.

Electric power is generally measured in watts (W), or joules per second. The electromagnetic-energy absorption rate in biological tissue, sometimes referred to as the specific absorption rate (SAR), indicates the energy per mass unit absorbed in the tissue and is usually expressed in units of watts per kilogram (W/kg), and may be expressed as $$SAR = \frac{1}{2}\frac{\sigma}{\rho}|E|^2, \qquad (1)$$

where $\sigma$ is the tissue electrical conductivity in units of Siemens per meter (S/m), $\rho$ is the tissue density in units of kilograms per cubic meter (kg/m³), and $|E|$ is the magnitude of the local electric field in units of volts per meter (V/m).

The relationship between the initial temperature rise $\Delta T$ (° C.) in tissue and the specific absorption rate may be expressed as $$\Delta T = \frac{1}{c} SAR \Delta t, \qquad (2)$$

where c is the specific heat of the tissue (in units of Joules/kg-° C.), and $\Delta t$ is the time period of exposure in seconds (sec). Substituting equation (1) into equation (2) yields a relation between the induced temperature rise in tissue and the applied electric field as $$\Delta T = \frac{1}{2}\frac{\sigma}{\rho c}|E|^2 \Delta t. \qquad (3)$$

As can be seen from the above equations, modifying the local electric-field amplitude directly affects the local energy absorption and induced temperature rise in tissue. In treatment methods such as hyperthermia therapy, it would be desirable to deposit an electric field of sufficient magnitude to heat malignant tissue to temperatures above 41° C. while limiting the SAR magnitude in nearby healthy tissue to be less than that within the tumor to keep the healthy cells below the temperature causing cell death. In existing, multiple, microwave applicator systems for hyperthermia treatment, the overall heating pattern produced by the multiple applicators may be a combination of the individual heating patterns produced by each separate applicator, or a result of the superposition of electromagnetic waves from all the applicators in the system.

Unfortunately, during certain procedures, clinicians cannot accurately predetermine or manually adjust the settings for output power and phase of multiple microwave applicators to focus heat reliably, making it difficult to determine the area or volume of tissue that will be ablated.

SUMMARY

The present disclosure relates to an electrosurgical system for directing energy to tissue including a generator assembly operable to supply power having a selected phase, amplitude and frequency, and an applicator array assembly. The applicator array assembly includes a shell assembly, a plurality of energy applicators disposed within the shell assembly, and a power divider unit electrically coupled to the generator assembly. The power divider unit is operable to divide power into the applicator array assembly.

The present disclosure also relates to a method for manufacturing an electrosurgical device including the initial steps of: providing a plurality of coaxial cables, each having an inner conductor, an outer conductor, and a dielectric material disposed therebetween; forming a plurality of first applicator segments by joining an electrically-conductive member to a distal end of the inner conductor of each of the plurality of coaxial cables; forming a plurality of second applicator segments by joining a balun structure to a distal portion of the outer conductor of each of the plurality of first applicator segments; forming a plurality of third applicator segments by positioning an electrically-conductive cylinder overlying a distal portion of the balun structure of each of the plurality of second applicator segments. The method also includes the step of forming a plurality of energy applicators by forming a dielectric structure having a proximal end disposed substantially adjacent to a distal end of the electrically-conductive cylinder of each of the plurality of third applicator segments. Each dielectric structure longitudinally extends from the distal end of the electrically-conductive cylinder to a distal end of the electrically-conductive member. The method also includes the steps of forming an applicator array assembly including the plurality of energy applicators and having a chamber disposed at least partially surrounding the plurality of energy applicators configured for circulating coolant fluid therebetween, and providing a power divider unit configured for dividing power for a plurality of channels connected to the applicator array assembly.

BRIEF DESCRIPTION OF THE DRAWINGS

Objects and features of the presently disclosed electromagnetic energy delivery devices will become apparent to those of ordinary skill in the art when descriptions of various embodiments thereof are read with reference to the accompanying drawings, of which.

DETAILED DESCRIPTION

Figure 1A:
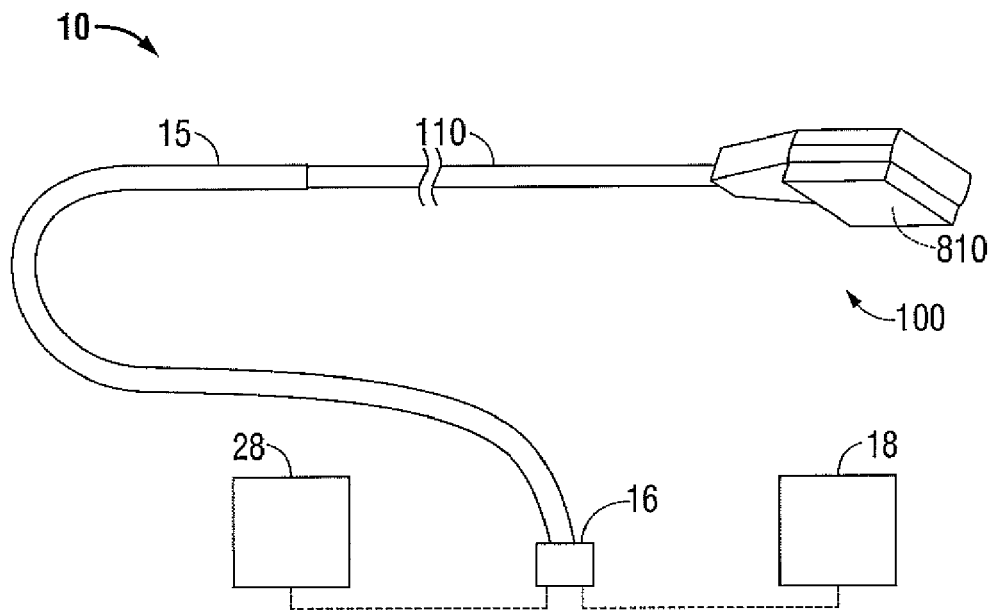
FIG. 1A is a schematic diagram of an ablation system according to an embodiment of the present disclosure.

Hereinafter, embodiments of the presently disclosed electromagnetic energy delivery device including an energy applicator array will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide electromagnetic energy delivery devices for treating tissue and methods of directing electromagnetic radiation to tissue. Embodiments may be implemented using electromagnetic radiation at microwave frequencies or at other frequencies. An electromagnetic energy delivery device including an energy applicator array, according to various embodiments, is designed and configured to operate between about 500 MHz and about 10 GHz with a directional radiation pattern.

Various embodiments of the presently disclosed electromagnetic energy delivery device including an energy applicator array are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1A shows an electrosurgical system 10, according to an embodiment of the present disclosure that includes an electromagnetic energy delivery device or ablation array assembly 100. An embodiment of an electromagnetic energy delivery device, such as the ablation array assembly 100 of FIG. 1A, in accordance with the present disclosure, is shown in more detail in FIGS. 9 through 11. It will be understood, however, that other electromagnetic energy delivery device embodiments may also be used.

Ablation array assembly 100, which is described in more detail later in this disclosure, generally includes an energy applicator array 810 having a radiating portion connected by a feedline 110 (or shaft) via a transmission line 15 to a connector 16, which may further operably connect the ablation array assembly 100 to a power generating source or generator assembly 28, e.g., a microwave or RF electrosurgical generator.

Feedline 110 may be formed from a suitable flexible, semi-rigid or rigid microwave conductive cable and may connect directly to an electrosurgical power generating source 28. Alternatively, the feedline 110 may electrically connect the energy applicator array 810 via the transmission line 15 to the electrosurgical power generating source 28. Feedline 110 may have a variable length from a proximal end of the energy applicator array 810 to a distal end of transmission line 15 ranging from a length of about one inch to about twelve inches. Feedline 110 may be formed of suitable electrically-conductive materials, e.g., copper, gold, silver or other conductive metals or metal alloys having similar conductivity values. Feedline 110 may be made of stainless steel, which generally offers the strength required to puncture tissue and/or skin. Conductive materials used to form the feedline 110 may be plated with other materials, e.g., other conductive materials, such as gold or silver, to improve their properties, e.g., to improve conductivity, decrease energy loss, etc. In some embodiments, the feedline 110 includes stainless steel, and to improve the conductivity thereof, the stainless steel may be coated with a layer of a conductive material such as copper or gold. Feedline 110 may include an inner conductor, a dielectric material coaxially surrounding the inner conductor, and an outer conductor coaxially surrounding the dielectric material. Feedline 110 may be cooled by fluid e.g., saline or water, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. An embodiment of a power generating source, such as the generator assembly 28 of FIG. 1A, in accordance with the present disclosure, is shown in more detail in FIG. 16. Transmission line 15 may additionally, or alternatively, provide a conduit (not shown) configured to provide coolant fluid from a coolant source 18 to one or more components of the ablation array assembly 100.

Figure 10:
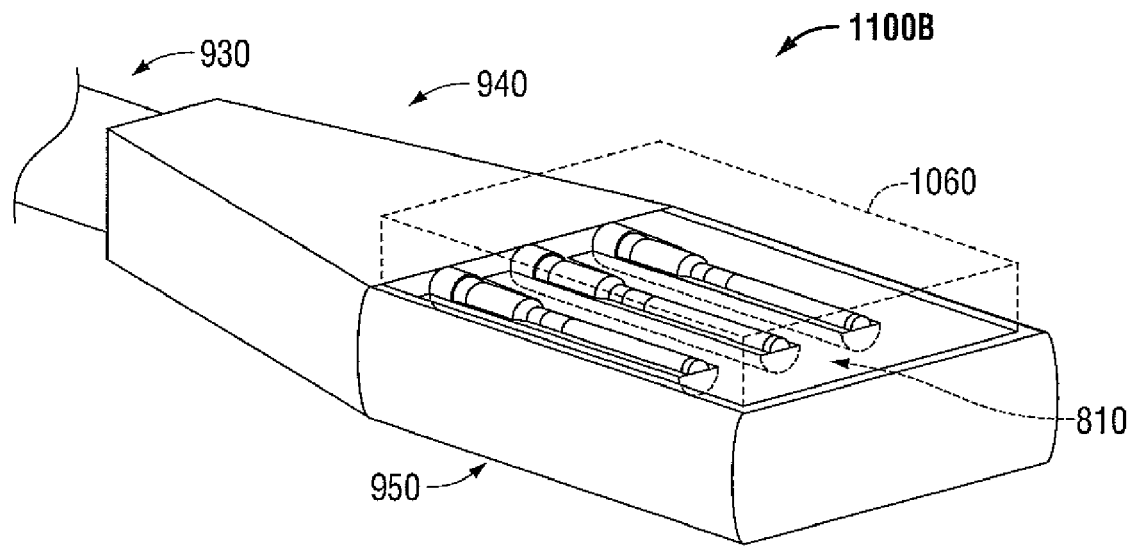
FIG. 10 is a perspective view of the portion of the energy delivery device of FIG. 9 shown with a cooling chamber according to an embodiment of the present disclosure.

In some embodiments, the ablation array assembly 100 may be provided with a coolant chamber (e.g., 1060 shown in FIG. 10). Additionally, the ablation array assembly 100 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

During microwave ablation, e.g., using the electrosurgical system 10, the electromagnetic energy delivery device 100 is inserted into or placed adjacent to tissue and microwave energy is supplied thereto. Ultrasound or computed tomography (CT) guidance may be used to accurately guide the ablation array assembly 100 into the area of tissue to be treated. Ablation array assembly 100 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the ablation array assembly 100 may depend on the progress of the heat distribution within the tissue area that is to be destroyed and/or the surrounding tissue. Single or multiple electromagnetic energy delivery devices 100 may provide ablations in short procedure times, e.g., a few minutes, to destroy cancerous cells in the target tissue region.

A plurality of electromagnetic energy delivery devices 100 may be placed in variously-arranged configurations to substantially simultaneously ablate a target tissue region, making faster procedures possible. Multiple electromagnetic energy delivery devices 100 can be used to synergistically create a large ablation or to ablate separate sites simultaneously. Tissue ablation size and geometry is influenced by a variety of factors, such as the energy applicator design, number of energy applicators used simultaneously, ablation time and wattage, and tissue characteristics.

Figure 1B:
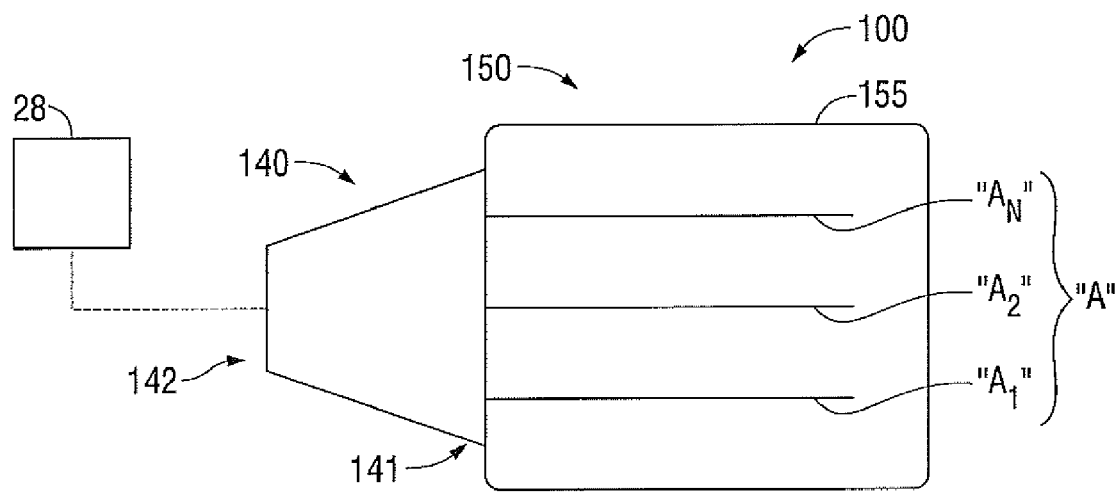
FIG. 1B is a schematic diagram of an embodiment of the electromagnetic energy delivery device of the ablation system of FIG. 1A in accordance with the present disclosure shown with an energy applicator array.

FIG. 1B schematically shows an embodiment of the electromagnetic energy delivery device 100 of the electrosurgical system 10 of FIG. 1A that includes an applicator array assembly 150, a generator assembly 28 that supplies power having a selected phase, amplitude and frequency, and a power divider unit 140 electrically coupled to the generator assembly 28 that divides power into the applicator array assembly 150. Power divider unit 140 generally divides power into a plurality of energy applicators (e.g., 270A, 270B, 270C shown in FIG. 19) of the applicator array assembly 150. In some embodiments, the applicator array assembly 150 and the power divider unit 140 are integrally formed. In embodiments, the applicator array assembly 150 includes a shell assembly 155 and an applicator array "A" that may include any "N" number of energy applicators (e.g., "$A_1$", "$A_2$" ... "$A_N$"), and may include a cooling chamber (e.g., 1060 shown in FIG. 10). Because of constructive interference of electric fields at the intended focus and destructive interference of electric fields away from the focus, geometrically-focused energy deposition from multiple electric fields emitted from the applicator array assembly 150, according to embodiments of the present disclosure, may improve localization of the absorbed energy in targeted tissue and focus heat reliably.

Power divider unit 140 generally divides power for a plurality of channels (e.g., 350A, 350B, 350C shown in FIG. 20) connected to the applicator array assembly 150, and may include a plurality of output ports (e.g., 448A, 448B, 448C shown in FIG. 21), wherein each output port may be connectable to any one or more of the energy applicators of the applicator array assembly 150. In some embodiments, the power divider unit 140 may include a plurality of phase shifters (e.g., 443A, 443B, 443C shown in FIG. 21). In some embodiments, the power divider unit 140 includes a phase-balanced microwave power splitter (e.g., 240 shown in FIG. 19), and may provide a substantially equal power split to the energy applicators of the applicator array assembly 150 while maintaining a phase balance of <+/−45 degrees. In an electrosurgical system (e.g., 10 shown in FIG. 1A) according to an embodiment of the present disclosure, a generator assembly (e.g., 28 shown in FIG. 1B) includes a processor (e.g., 82 shown in FIG. 17) that is operably coupled to one or more phase monitor units (e.g., 447A, 447B, 447C shown in FIG. 21) of the power divider unit 140.

Power divider unit 140 may be a power splitter configured to split an input signal from the generator assembly 28 into two or more equal phase output signals, such as a Wilkinson power splitter. Power divider unit 140 may be implemented by any suitable power divider that provides equal or unequal power split at the output ports of the power divider unit 140. Power divider unit 140 may maintain phase and/or amplitude balance. For example, the power divider unit 140 may be implemented using a 2-way power divider that provides equal or unequal power split at its output ports while maintaining a phase balance of <+/−45 degrees. Examples of power divider embodiments are disclosed in commonly assigned U.S. patent application Ser. No. 12/562,842 filed on Sept. 18, 2009, entitled "TISSUE ABLATION SYSTEM WITH ENERGY DISTRIBUTION". In embodiments, the power divider unit 140 may include a controller (e.g., 330 shown in FIG. 20).

Power divider unit 140, according to various embodiments, may deliver microwave power to particular channels individually or any combination of one or more channels equally or unequally to facilitate selective activation of energy delivery to particular channels or combination of channels. For example, a user may select channels to which energy is delivered. In this scenario, if the second and third channels are selected, energy delivery may be divided equally between the second and third channels and, thus, unequally between the first channel and the second and third channels since no energy is delivered to the first channel in this scenario. Further, in this scenario, energy may be delivered to individual channels according to selected time intervals by dynamically changing the channels to which energy is delivered. For example, energy may be delivered to the first channel at a time interval, t1. At a subsequent time interval, t2, energy is delivered to the first channel and the third channel. At a subsequent time interval, t3, energy delivery to the first channel is stopped and energy delivery to the third channel continues. At a subsequent time interval, t4, energy delivery to all channels is stopped. In some embodiments, the power divider unit 140 may divide energy between the energy applicators (e.g., "$A_1$", "$A_2$", "$A_N$" shown in FIG. 1B) to tailor the size and shape of ablation lesions.

Applicator array assembly 150, according to various embodiments, includes a plurality of input ports (not shown) connectable to any one or more output ports (not shown) of the power divider unit 140, and may be disposed substantially adjacent to a distal end portion 141 of the power divider unit 140. In some embodiments, a handle assembly (not shown) may be attached to the proximal end portion 142 of the power divider unit 140, and may be coaxially-disposed around at least a portion of the feedline 110. The shape and size of the power divider unit 140 and the applicator array assembly 150 may be varied from the configuration depicted in FIG. 1B.

Figure 2:
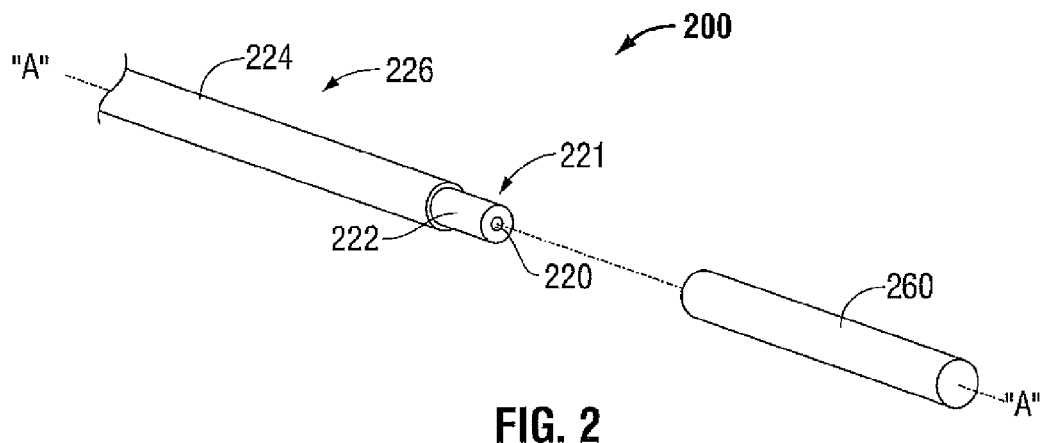
FIG. 2 is a perspective view with parts disassembled of a portion of an energy applicator according to an embodiment of the present disclosure.
Figure 6:
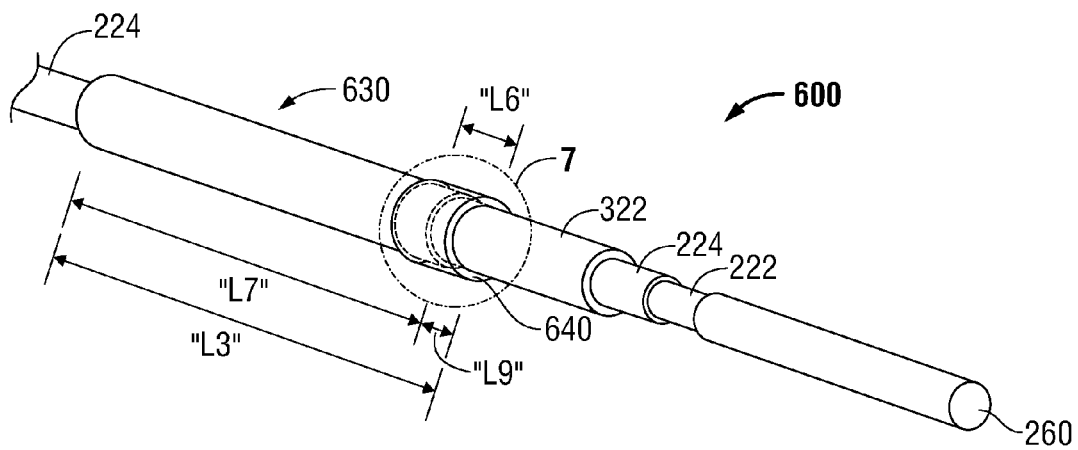
FIG. 6 is a perspective view of the portion of the energy applicator of FIG. 3 shown with another embodiment of an electrically-conductive layer and an electrically-conductive cylinder in accordance with the present disclosure.
Figure 7:
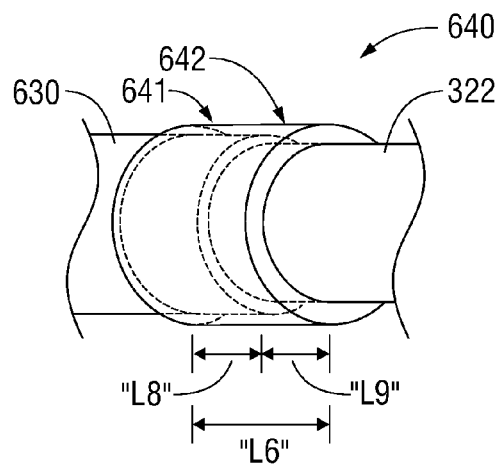
FIG. 7 is an enlarged view of the indicated area of detail of FIG. 6 according to an embodiment of the present disclosure.
Figure 8:
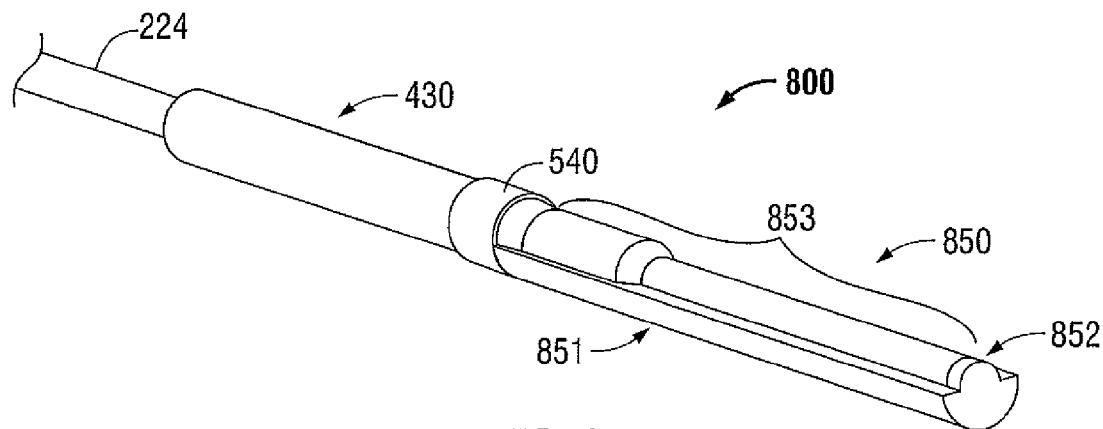
FIG. 8 is a perspective view of the portion of the energy applicator of FIG. 5 shown with a dielectric structure disposed distal to the electrically-conductive cylinder according to an embodiment of the present disclosure.

FIGS. 2 through 8 show a sequentially-illustrated, assembly of components forming an energy applicator, shown generally as 800 in FIG. 8, in accordance with the present disclosure. In FIG. 2, a coaxial feedline 226 is shown with the outer conductor 224 trimmed back, such that a portion 221 of the dielectric material 222 and the inner conductor 220 extends beyond the outer conductor 224. According to an embodiment of the present disclosure, an energy applicator segment (shown generally as 200 in FIG. 2) includes an electrically-conductive element 260 that extends along the longitudinal axis "A" of the energy applicator segment 200. Electrically-conductive element 260 may be positioned in a distal portion of the energy applicator 800. In some embodiments, the electrically-conductive member 260 is a solid metal cylinder disposed at the distal end of the portion 221 electrically coupled to the inner conductor 220 (e.g., by solder). Electrically-conductive element 260 may be formed of any suitable electrically-conductive material (e.g., metal such as stainless steel, aluminum, titanium, copper, etc.) of any suitable length. The shape and size of the electrically-conductive element 260 may be varied from the configuration depicted in FIG. 2.

Figure 3:
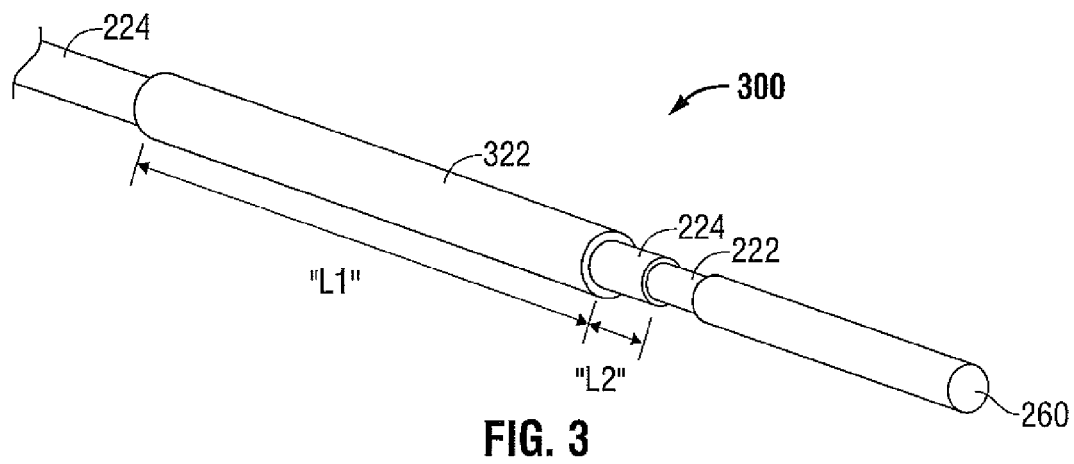
FIG. 3 is a perspective, assembled view of the portion of the energy applicator of FIG. 2 shown with a dielectric layer disposed about a portion of the outer conductor according to an embodiment of the present disclosure.

FIG. 3 shows an energy applicator segment 300 according to an embodiment of the present disclosure that is similar to the energy applicator segment 200 of FIG. 2, except for a dielectric layer 322 (also referred to herein as a balun insulator) disposed coaxially about a distal portion of the outer conductor 224 of the feedline 226. Dielectric layer 322 may have a suitable length "L1" in a range of about 0.1 inches to about 3.0 inches. Dielectric layer 322 may be spaced apart from and disposed proximal to the distal end of the outer conductor 224. In some embodiments, the dielectric layer 322 is spaced apart, by a length "L2", e.g., about 0.1 inches, from the distal end of the outer conductor 224. Balun insulator 322 may extend distally beyond the distal end of the conductive balun sleeve (e.g., 430 shown in FIG. 4) to direct current into a balancing/unbalancing (balun) structure (e.g., "B" shown in FIG. 4). Dielectric layer 322 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. Dielectric layer 322 may be grown, deposited or formed by any other suitable technique. In some embodiments, the balun insulator 322 is formed from a material with a dielectric constant in the range of about 1.7 to about 10. The shape, size and relative position of the balun insulator 322 may be varied from the configuration depicted in FIG. 3.

Figure 4:
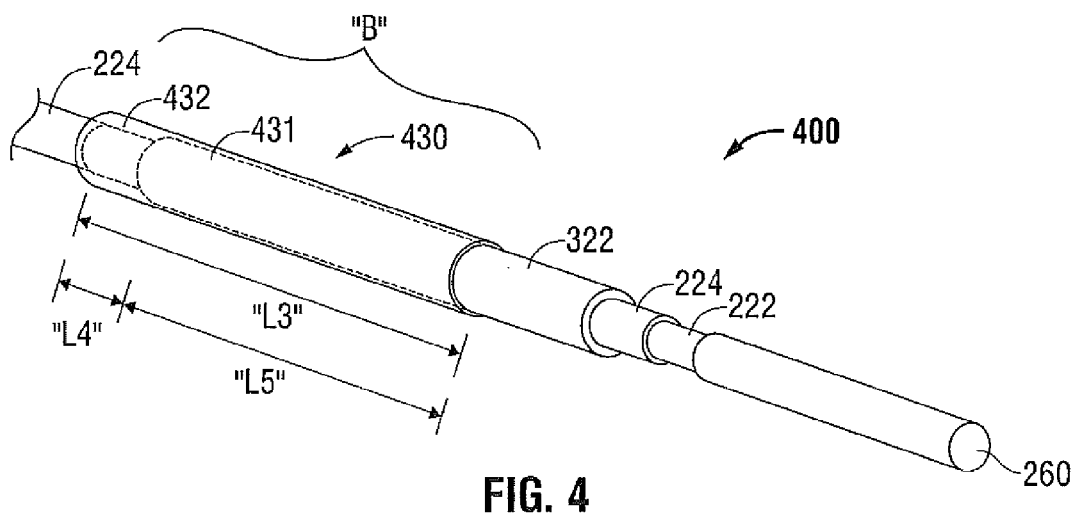
FIG. 4 is a perspective view of the portion of the energy applicator of FIG. 3 shown with an electrically-conductive layer disposed about a portion of the dielectric layer according to an embodiment of the present disclosure.

FIG. 4 shows an energy applicator segment 400 according to an embodiment of the present disclosure that is similar to the energy applicator segment 300 of FIG. 3 except for an electrically-conductive layer 430 (also referred to herein as a conductive balun sleeve) disposed coaxially about a proximal portion of the energy applicator segment 400. Electrically-conductive layer 430 may have any suitable length "L3", e.g., about 0.1 inches to about 3.0 inches. Electrically-conductive layer 430 may be formed as a single structure and electrically coupled to the outer conductor 224, e.g., by solder or other suitable electrical connection. In some embodiments, the electrically-conductive layer 430 includes a first portion 431, having a length "L5", disposed coaxially about a proximal portion of the dielectric layer 322, and a second portion 432, having a length "L4", disposed proximally to the first portion 431 electrically coupled to the outer conductor 224. First and second portions 431, 432 may be formed of any suitable electrically-conductive material, e.g., metal such as stainless steel, titanium, copper, etc., and may be formed in any suitable manner. First and second portions 431, 432 may be formed separately from each other. First and second portions 431, 432 may form a single, unitary structure. The shape and size of the electrically-conductive balun sleeve 430 may be varied from the configuration depicted in FIG. 4.

Figure 5:
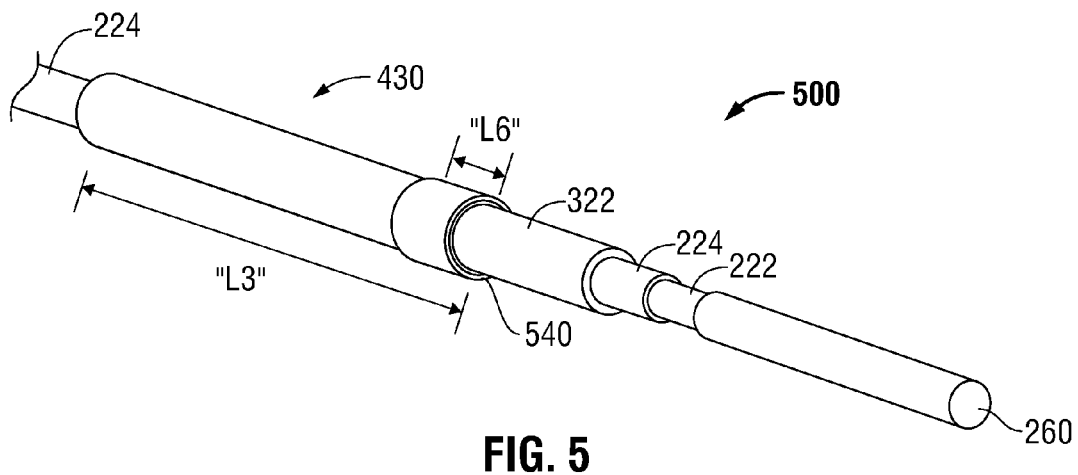
FIG. 5 is a perspective view of the portion of the energy applicator of FIG. 4 shown with an electrically-conductive cylinder disposed about the distal end of the electrically-conductive layer according to an embodiment of the present disclosure.

FIG. 5 shows an energy applicator segment 500 according to an embodiment of the present disclosure that is similar to the energy applicator segment 400 of FIG. 4, except for an electrically-conductive cylinder 540 disposed coaxially about a distal portion of the electrically-conductive layer 430. Electrically-conductive cylinder 540 may have a suitable length "L6" in a range of about 0.05 inches to about 0.2 inches. In some embodiments, the distal edge of electrically-conductive cylinder 540 is disposed overlying the distal edge of the electrically-conductive layer 430. The shape and size of the electrically-conductive cylinder 540 may be varied from the configuration depicted in FIG. 5.

FIG. 6 shows an energy applicator segment 600 according to an embodiment of the present disclosure that includes an electrically-conductive layer 630 and an electrically-conductive cylinder 640. Electrically-conductive layer 630 surrounds a proximal portion of the dielectric layer 322 and is electrically coupled to the outer conductor 224, e.g., by solder or other suitable electrical connection. Electrically-conductive layer 630 is similar to the electrically-conductive layer 430 of FIG. 4, except that the electrically-conductive layer 630 has a length that is less than the length "L3" of the electrically-conductive layer 430. As shown in FIG. 6, the electrically-conductive layer 630 may have a length "L7", which is shorter than the length "L3" by a length "L9".

Electrically-conductive cylinder 640 shown in FIGS. 6 and 7 is similar to the electrically-conductive cylinder 540 of FIG. 5, except that the electrically-conductive cylinder 640 extends distally beyond the distal edge of the electrically-conductive layer 630. As shown in FIG. 7, the electrically-conductive cylinder 640, having a length "L6", includes a first portion 641, having a length "L8", disposed coaxially about the distal end of the electrically-conductive layer 630, and a second portion 642, having a length "L9", disposed distally to the first portion 641, surrounding a portion of the dielectric layer 322 distally extending beyond the electrically-conductive layer 630. In some embodiments, the electrically-conductive cylinder 640 is positioned relative to the distal edge of the electrically-conductive layer 630 such that the combined length of the electrically-conductive layer 630 and the electrically-conductive cylinder 640 is a length "L3", which may be, for example, a quarter wavelength or a half wavelength. The shape and size of the electrically-conductive cylinder 640 may be varied from the configuration depicted in FIGS. 6 and 7.

FIG. 8 shows an energy applicator segment 800 according to an embodiment of the present disclosure that is similar to the energy applicator segment 500 of FIG. 5, except for a generally longitudinally-disposed dielectric structure 850. In some embodiments, the dielectric structure 850 includes a dielectric cap configured to cover the distal end of the electrically-conductive member 260.

As shown in FIG. 8, the dielectric structure 850 may be disposed distally to the electrically-conductive cylinder 540. Dielectric structure 850 may be formed using over-molding techniques or other forming techniques. In some embodiments, the dielectric structure 850 is formed from a material with a dielectric constant in the range of about 1.7 to about 10.

The shape and size of the dielectric structure 850 may be varied from the configuration depicted in FIG. 8.

In some embodiments, the dielectric structure 850 includes a first dielectric segment 851, a second dielectric segment 852, and a third dielectric segment 853. As shown in FIG. 8, the first dielectric segment 851 extends distally from the distal end of the electrically-conductive cylinder 540 and may have a substantially half-cylindrical shape. First dielectric segment 851 may be made to encompass any radial angle. In some embodiments, the fist dielectric segment 851 extends from the distal end of the electrically-conductive cylinder 540 to distal end of the electrically-conductive member 260. Second dielectric segment 852 is configured to cover the distal end of the electrically-conductive member 260, and may include a first portion and a second portion. In some embodiments, the first and second dielectric segments 851, 852 are integrally formed in a molding process. First dielectric segment 851, the second dielectric segment 852 and the third dielectric segment 853 may be formed by any suitable process.

In some embodiments, the energy applicator segment 800 may be provided with an outer jacket (not shown) disposed about the electrically-conductive layer 430, the electrically-conductive cylinder 540 and/or the dielectric structure 850. The outer jacket may be formed of any suitable material, such as, for example, polymeric or ceramic materials. The outer jacket may be applied by any suitable method, such as, for example, heat shrinking, over-molding, coating, spraying dipping, powder coating, baking and/or film deposition. The outer jacket may be a water-cooled catheter formed of a material having low electrical conductivity.

Figure 9:
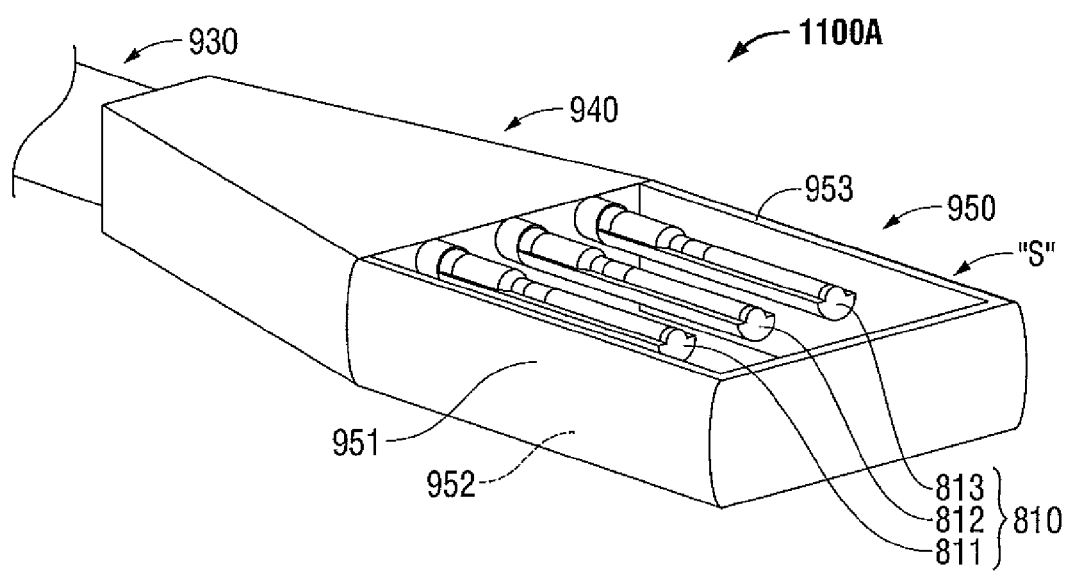
FIG. 9 is a perspective view of a portion of an energy delivery device that includes an array of energy applicators, such as the energy applicator of FIG. 8, in accordance with the present disclosure.
Figure 11:
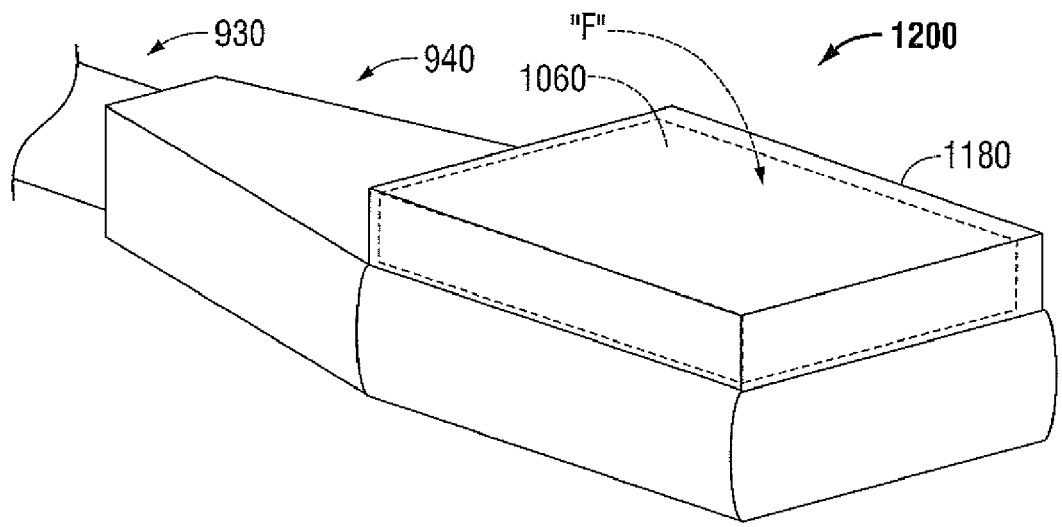
FIG. 11 is a perspective view of the portion of the electromagnetic energy delivery device of FIG. 10 shown with a material disposed about the cooling chamber according to an embodiment of the present disclosure.

FIG. 9 shows a portion or unit 1100A of an electromagnetic energy delivery device, such the electromagnetic energy delivery device 1200 of FIG. 11, with an array of three energy applicators, such as the energy applicator 800 of FIG. 8, in accordance with the present disclosure. As shown in FIG. 9, the portion 1100A includes an applicator array assembly 950, a power divider unit 940 electrically coupleable to a generator assembly (e.g., 28 shown in FIG. 16) for dividing power for a plurality of channels (e.g., 450A, 450B and 450C shown in FIG. 21) connected to the applicator array assembly 950, and a handle member 930. Power divider unit 940 is similar to the power divider unit 140 of FIG. 1B and further description thereof is omitted in the interests of brevity.

In embodiments, the applicator array assembly 950 includes a shell assembly 953 and an applicator array 810 including three energy applicators 811, 812 and 813. In embodiments, the shell assembly 953 has a substantially rectangular shape, and may extend distally beyond the length of the radiating portion of the applicator array 810. The shape and size of the shell assembly 953 may be varied from the configuration depicted in FIG. 9. In some embodiments, the shell assembly 953 has a substantially oblong shape. Although the portion 1100A of the electromagnetic energy delivery device illustrated in FIG. 9 includes three energy applicators 811, 812 and 813, it is to be understood that any "N" number of energy applicators may be utilized.

Shell assembly 953 may include an outer portion 951 and an inner portion 952. In some embodiments, the outer portion 951 of the shell assembly 953 is formed of an electrically-conductive material e.g., stainless steel, and electrically coupled to the distal end of the conductive balun sleeve (e.g., 430 shown in FIG. 4) of one or more of the energy applicators 811, 812 and 813. Inner portion 952 of the shell assembly 953 may be formed of any suitable dielectric material. A distal portion of the inner portion 952 may extend distal to the distal ends of the energy applicators 811, 812 and 813.

Outer portion 951 may include any electrically-conductive material, such as, for example, copper, stainless steel, titanium, titanium alloys such as nickel-titanium and titanium-aluminum-vanadium alloys, aluminum, aluminum alloys, tungsten carbide alloys or combinations thereof. Portions of the outer portion 951 may be loaded with low- to mid-range permittivity dielectric materials to aid in radiation directivity and impedance matching. Several shells, or other shapes, of different dielectric materials may nest together to form the outer portion 951.

Inner portion 952 may include a dielectric material. In some embodiments, the inner portion 952 includes dielectric material layers. For example, the inner portion 952 may include one or more thin layers, one or more thick layers or a mixture of thick and thin layers. Inner portion 952 may be composed of any suitable dielectric material which may be the same as, or different from, the dielectric material, if any, used in the outer portion 951. The dielectric materials used to form the inner portion 952 may vary in dielectric constant with shells or more complex dielectric layering to achieve the optimum antenna directivity and energy to tissue delivery. In some embodiments, a portion of the cap of dielectric material 852 and a portion of the first dielectric segment 851 of one or more of the energy applicators 811, 812 and 813 are disposed in a recess in the form of a groove (not shown) defined in the planar top surface "S" of the inner portion 952. In some embodiments, the inner portion 952, or portions thereof, may be adapted to circulate coolant fluid therethrough.

FIG. 10 shows a portion 1100B of an electromagnetic energy delivery device according to an embodiment of the present disclosure that is similar to the portion 1100A of FIG. 9, except for a chamber 1060 (also referred to herein as a cooling chamber). Chamber 1060 generally includes a fluid inlet port (not shown) and a fluid outlet port (not shown). Coolant chamber 1060 is adapted to circulate coolant fluid (e.g., "F" shown in FIG. 11) therethrough, and may include baffles, multiple lumens, flow restricting devices, or other structures that may redirect, concentrate, or disperse flow depending on their shape.

FIG. 11 shows an embodiment of an electromagnetic energy delivery device 1200 in accordance with the present disclosure that includes the portion 1100B of FIG. 10 shown with a material 1180 disposed about the cooling chamber 1060 thereof. Material 1180 may include any suitable material. Suitable materials for use as the material 1180 may include high dielectric-constant materials, such as, for example, inorganic nonmetallic materials (e.g., ceramics), metallic oxides (e.g., alumina, titanium dioxide, zirconium dioxide, or zinc oxide) and combinations thereof. Material 1180 may include a nonconductive radio frequency transparent material, e.g., a glass fiber epoxy composite polyimide, high temperature conformable rubber or plastic. Material 1180 may be formed using over-molding techniques or other forming techniques.

Figure 12:
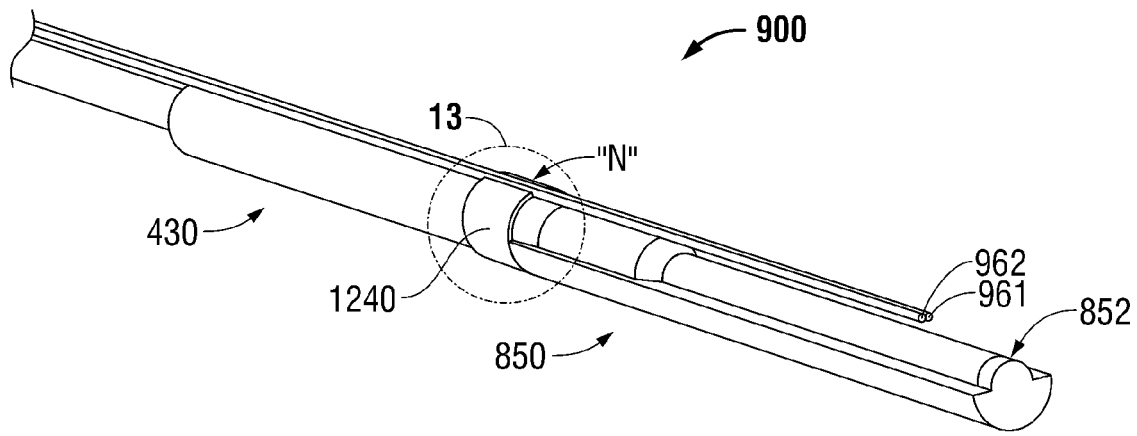
FIG. 12 is a perspective view of the portion of the energy applicator of FIG. 8 shown with a fluid inflow tube and a fluid outflow tube according to an embodiment of the present disclosure.

FIG. 12 shows an energy applicator segment 900 according to an embodiment of the present disclosure that is similar to the energy applicator segment 800 of FIG. 8, except for a longitudinally-extending inflow tube 961, a longitudinally-extending outflow tube 962, and an electrically-conductive cylinder 1240 having a notch "N" defined therein that is configured to receive the inflow and outflow tubes 961, 962. In some embodiments, the inflow and outflow tubes 961, 962 are configured to supply and/or dispense coolant fluid (e.g., saline, water or other suitable coolant fluid) into and out of a distal portion of a cooling chamber (e.g., 1560 shown in FIG. 15). A pump (not shown) may be connected in fluid communication between the cooling chamber and a coolant source (e.g., 18 shown in FIG. 1A). Inflow and outflow tubes 961, 962 may include thin-walled polyimide tubes. In some embodiments, a pump supplies coolant fluid from a coolant source to one or more inflow tubes 961 which, in turn, deliver coolant fluid to the cooling chamber (e.g., 1560 shown in FIG. 15). Additionally, or alternatively, a pump may be fluidly coupled to one or more outflow tubes 962 to draw coolant fluid out of the cooling chamber.

Figure 13:
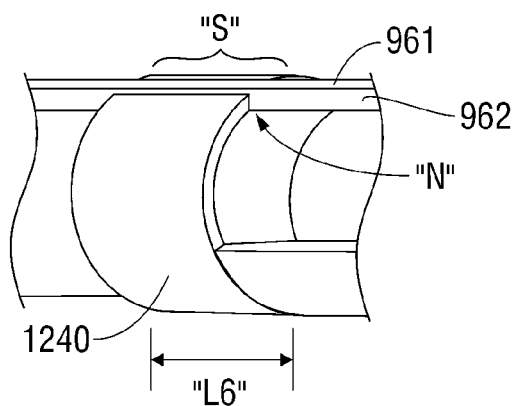
FIG. 13 is an enlarged view of the indicated area of detail of FIG. 12 according to an embodiment of the present disclosure.

As shown in FIGS. 12 and 13, the inflow and outflow tubes 961, 962 may extend longitudinally across the full length of the electrically-conductive layer 430 and at least partially across the dielectric structure 850. As shown in FIG. 13, a portion or segment "S" of the inflow and outflow tubes 961, 962 is disposed within a notch "N" defined within the electrically-conductive cylinder 1240. In some embodiments, the notch "N" is configured as a recess, e.g., in the form of a groove or hole. In other embodiments, the notch "N" is configured as a first recess (not shown) and a second recess (not shown), wherein the first recess is configured to receive one or more inflow tubes 961 and the second recess is configured to receive one or more outflow tubes 962.

Inflow tube 961 and the outflow tube 962 may be formed to have the same diameters or different diameters. Inflow and outflow tubes 961, 962 may have any suitable length. In some embodiments, the segment "S" of the inflow and outflow tubes 961, 962 is disposed between the electrically-conductive layer 430 and the outer circumferential surface of the electrically-conductive cylinder 1240, which helps minimize the outer diameter of the energy applicator. Inflow and outflow tubes 961, 962 may be held in place, e.g., along the electrically-conductive layer 430 and/or within the notch "N", by using UV adhesive or other similar suitable adhesives, as well as heat shrink tubing or by other suitable methods. The shape and size of the inflow and outflow tubes 961, 962, the electrically-conductive cylinder 1240 and the notch "N" may be varied from the configurations depicted in FIGS. 12 and 13.

Figure 14:
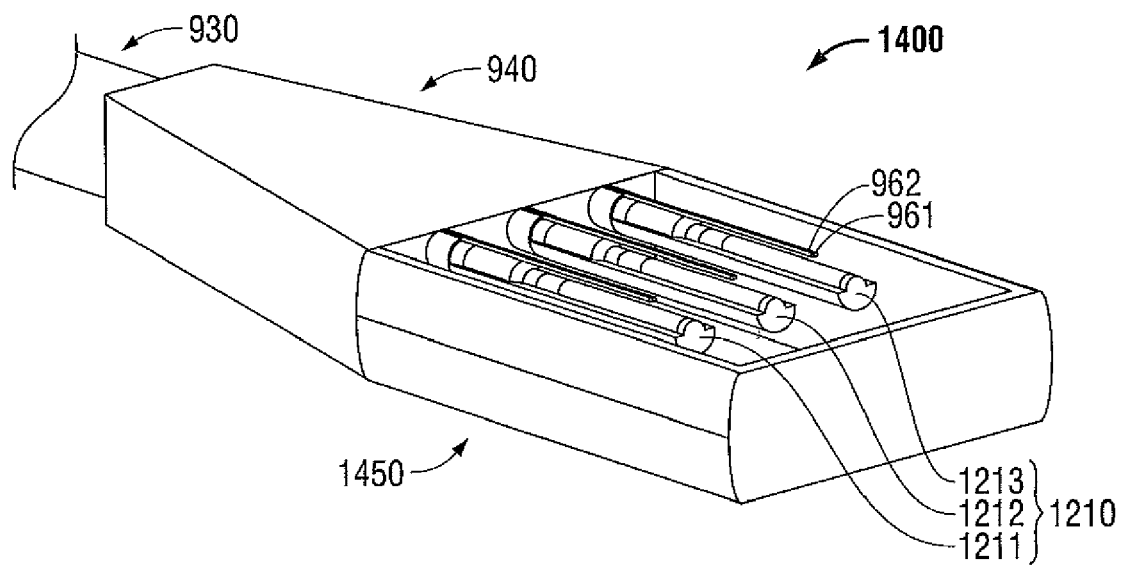
FIG. 14 is a perspective view of a portion of an electromagnetic energy delivery device with an array of three energy applicators, such as the energy applicator of FIG. 12, in accordance with the present disclosure.

FIG. 14 shows a portion 1400, of an electromagnetic energy delivery device that is similar to the portion 1100A of the electromagnetic energy delivery device of FIG. 9. As shown in FIG. 14, the portion 1400 includes an applicator array assembly 1450, a power divider unit 940 electrically coupleable to a generator assembly (e.g., 28 shown in FIG. 16) for dividing power for a plurality of channels connected to the applicator array assembly 1450, and a handle member 930. Power divider unit 940 is similar to the power divider unit 140 of FIG. 1B and further description thereof is omitted in the interests of brevity. Applicator array assembly 1450 is similar to the applicator array assembly 950 shown in FIG. 9, except for the inflow and outflow tubes 961 and 962, respectively. In some embodiments, the inflow and outflow tubes 961, 962 are configured to supply and/or dispense coolant fluid "F" (e.g., saline, water or other suitable coolant fluid) into and out of a cooling chamber (e.g., 1560 shown in FIG. 15).

Figure 15:
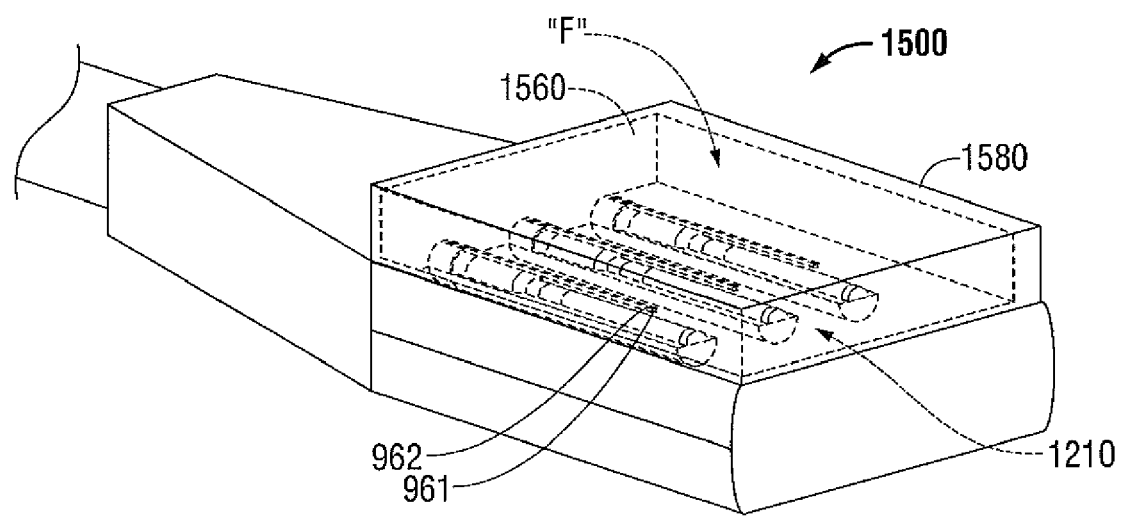
FIG. 15 is a perspective view of the portion of the electromagnetic energy delivery device of FIG. 14 shown with a cooling chamber and a material disposed thereabout according to an embodiment of the present disclosure.

FIG. 15 shows an embodiment of an electromagnetic energy delivery device 1500 in accordance with the present disclosure that includes the portion 1400 of FIG. 14 shown with a cooling chamber 1560 and a material 1580 disposed thereabout. Cooling chamber 1560 at least partially surrounds the energy applicator array 1210 including three energy applicators 1211, 1212 and 1213 (FIG. 14). The shape and size of the inflow and outflow tubes 961, 962 and the chamber 1560 may be varied from the configuration depicted in FIG. 15. In some embodiments, portions of the inflow and outflow tubes 961, 962 are disposed within the chamber 1560. Additionally, or alternatively, the chamber 1560 may include a material having a high dielectric constant, such as alumina, titanium dioxide or zirconium dioxide, for improved antenna directivity and energy to tissue delivery efficiency. Cooling chamber 1560 and the material 1580 disposed thereabout are similar to the chamber 1060 and the material 1080 shown in FIGS. 10 and 11, respectively, and further description thereof is omitted in the interests of brevity.

Figure 16:
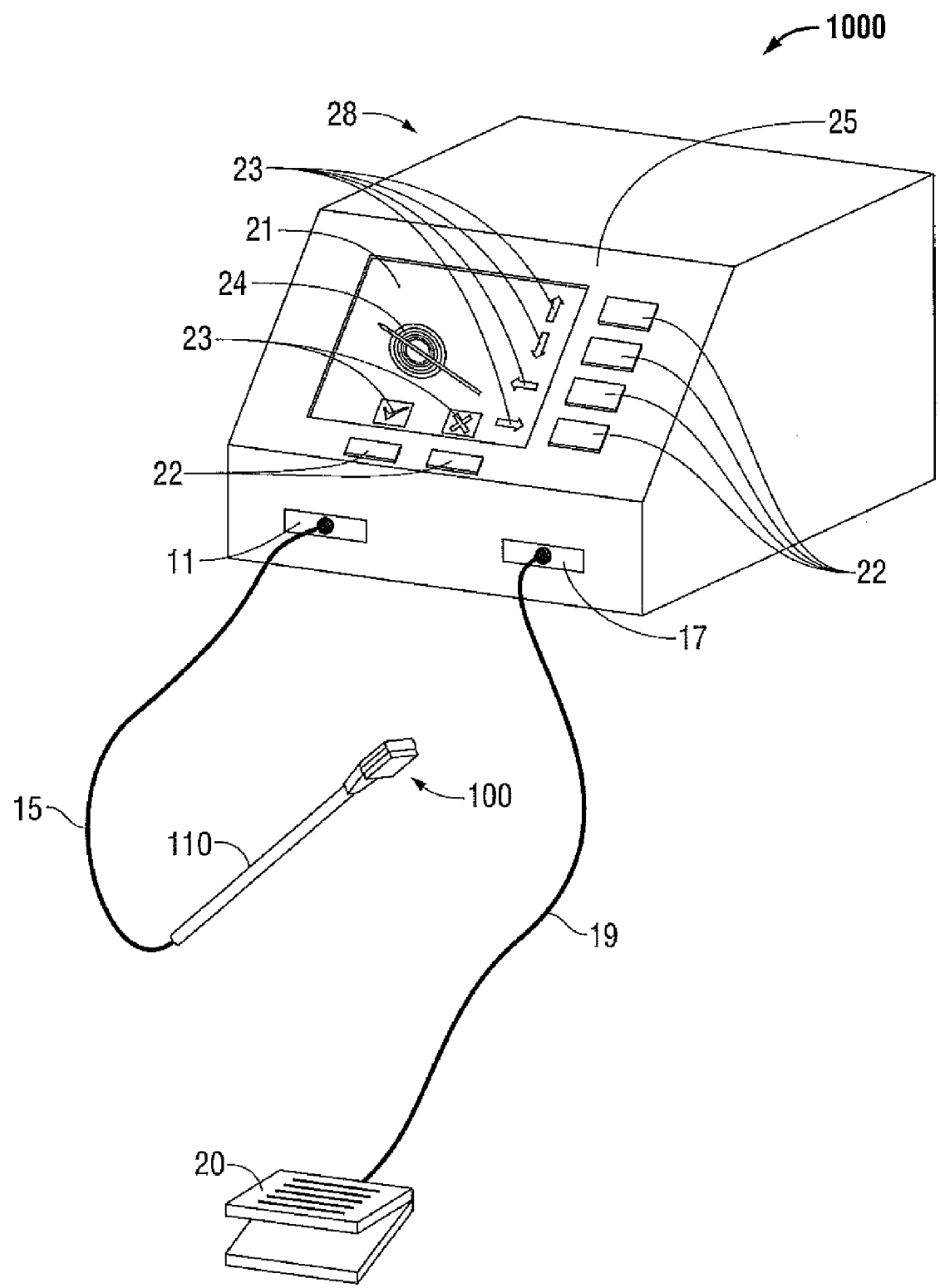
FIG. 16 shows a diagram of a microwave ablation system that includes a user interface for displaying and controlling ablation patterns in accordance with the present disclosure.

FIG. 16 schematically illustrates an electrosurgical system 1000 in accordance with an embodiment of the present disclosure. Electrosurgical system 1000 includes an actuator 20 operably coupled by a cable 19 via connector 17 to an embodiment of the generator assembly 28 of the electrosurgical system 10 of FIG. 1A. Actuator 20 may be a footswitch, a handswitch, a bite-activated switch, or any other suitable actuator. Cable 19 may include one or more electrical conductors for conveying an actuation signal from the actuator 20 to the generator assembly 28. In an embodiment, the actuator 20 is operably coupled to the generator assembly 28 by a wireless link, such as without limitation, a radiofrequency or infrared link. In use, the clinician may interact with the user interface 25 to preview operational characteristics of the electromagnetic energy delivery device 100.

Generator assembly 28, according to various embodiments, includes a generator module (e.g., 86 shown in FIG. 17) in operable communication with a processor (e.g., 82 shown in FIG. 17), a user interface 25, and an actuator 20. Electromagnetic energy delivery device 100 is operably coupled to an energy output of the generator module, which may be configured as a source of RF and/or microwave energy. Actuator 20 is operably coupled to the processor 82 via user interface 25. In embodiments, actuator 20 may be operably coupled to the processor and/or to the generator module by a cable connection, or a wireless connection.

User interface 25 may include a display 21, such as without limitation a flat panel graphic LCD (liquid crystal display), adapted to visually display at least one user interface element 23, 24. In an embodiment, display 21 includes touchscreen capability (not shown), e.g., the ability to receive input from an object in physical contact with the display, such as without limitation, a stylus or a user's fingertip. A user interface element 23, 24 may have a corresponding active region, such that, by touching the screen within the active region associated with the user interface element, an input associated with the user interface element 23, 24 is received by the user interface 25.

User interface 25 may additionally, or alternatively, include one or more controls 22 that may include without limitation a switch (e.g., pushbutton switch, toggle switch, slide switch) and/or a continuous actuator (e.g., rotary or linear potentiometer, rotary or linear encoder.) In an embodiment, a control 22 has a dedicated function, e.g., display contrast, power on/off, and the like. Control 22 may also have a function that may vary in accordance with an operational mode of the electrosurgical system 10. A user interface element 23 may be positioned substantially adjacently to control 22 to indicate the function thereof. Control 22 may also include an indicator, such as an illuminated indicator (e.g., a single- or variably-colored LED indicator.)

Figure 17:
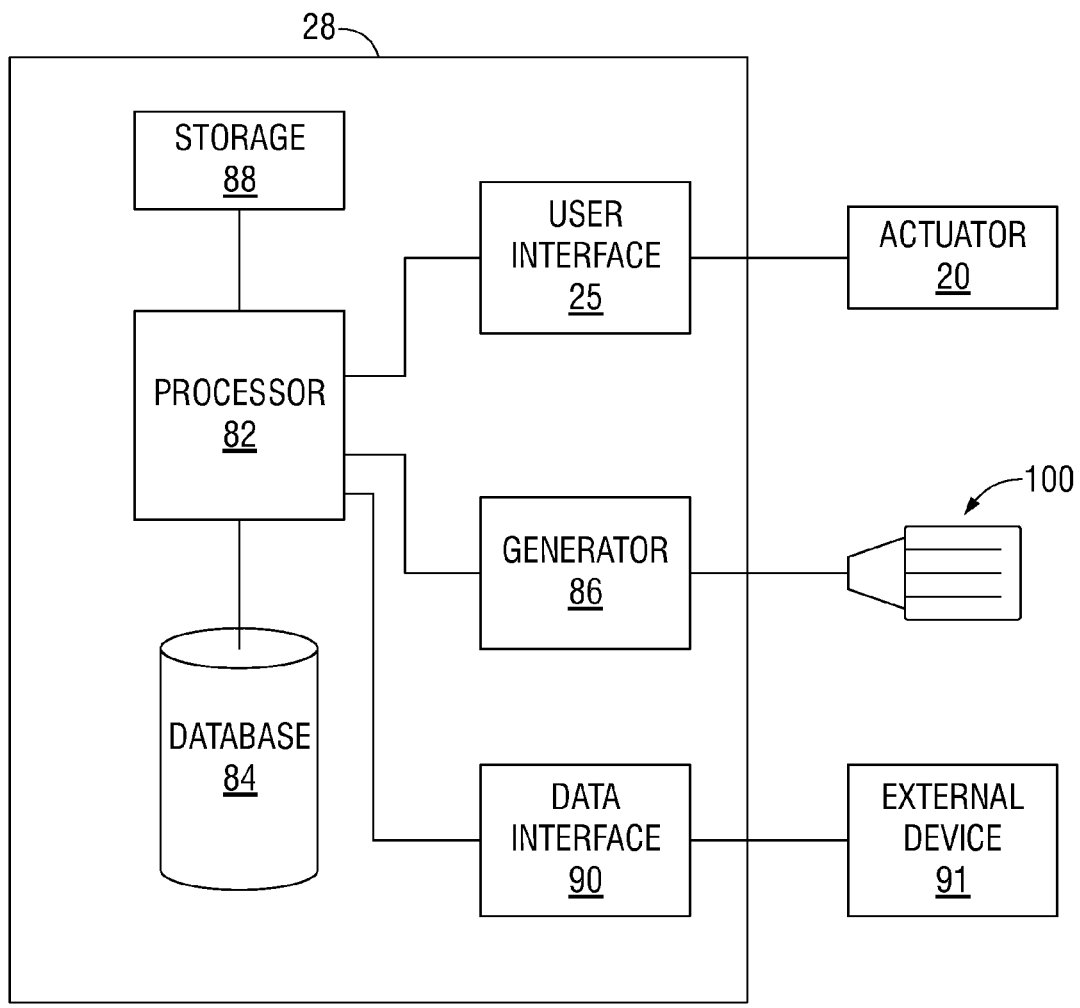
FIG. 17 is a block diagram of a microwave ablation system in accordance with the present disclosure.

FIG. 17 is a block diagram showing one embodiment of the electrosurgical system 1000 of FIG. 16. In an embodiment, the generator module 86 is configured to provide energy of about 915 MHz. Generator module 86 may additionally, or alternatively, be configured to provide energy of about 2450 MHz (2.45 GHz). The present disclosure contemplates embodiments wherein the generator module 86 is configured to generate a frequency other than about 915 MHz or about 2450 MHz, and embodiments wherein the generator module

86 is configured to generate variable frequency energy. Generator assembly 28 includes a processor 82 that is operably coupled to user interface 21. Processor 82 may include any type of computing device, computational circuit, or any type of processor or processing circuit capable of executing a series of instructions that are stored in a memory, e.g., storage device 88 or external device 91.

In some embodiments, a storage device 88 is operably coupled to the processor 82, and may include random-access memory (RAM), read-only memory (ROM), and/or non-volatile memory (NV-RAM, Flash, and disc-based storage.) Storage device 88 may include a set of program instructions executable on the processor 82 for executing a method for displaying and controlling ablation patterns in accordance with the present disclosure. Generator assembly 28 may include a data interface 90 that is configured to provide a communications link to an external device 91. In an embodiment, the data interface 90 may be any of a USB interface, a memory card slot (e.g., SD slot), and/or a network interface (e.g., 100BaseT Ethernet interface or an 802.11 "Wi-Fi" interface.) External device 91 may be any of a USB device (e.g., a memory stick), a memory card (e.g., an SD card), and/or a network-connected device (e.g., computer or server).

Generator assembly 28 may also include a database 84 that is configured to store and retrieve energy applicator data, e.g., parameters associated with one or energy applicators (e.g., "$A_1$", "$A_2$", "$A_N$" shown in FIG. 1B) and/or one or more applicator array assemblies (e.g., 150 shown in FIG. 1B). Parameters stored in the database 84 in connection with an applicator array assembly may include, but are not limited to, applicator array assembly identifier, applicator array assembly dimensions, a frequency, an ablation length, an ablation diameter, a temporal coefficient, a shape metric, and/or a frequency metric. In an embodiment, ablation pattern topology may be included in the database 84, e.g., a wireframe model of an applicator array assembly (e.g., 150 shown in FIG. 1B) and/or an ablation pattern associated therewith.

Database 84 may also be maintained at least in part by data provided by the external device 91 via the data interface 90. For example without limitation, energy applicator data may be uploaded from an external device 91 to the database 84 via the data interface 90. Energy applicator data may additionally, or alternatively, be manipulated, e.g., added, modified, or deleted, in accordance with data and/or instructions stored on the external device 91. In an embodiment, the set of energy applicator data represented in the database 84 is automatically synchronized with corresponding data contained in external device 91 in response to external device 91 being coupled (e.g., physical coupling and/or logical coupling) to data interface 90.

Processor 82 is programmed to enable a user, via user interface 25 and/or display 21, to view at least one ablation pattern and/or other energy applicator data corresponding to an embodiment of an applicator array assembly. For example, a surgeon may determine that a substantially spherical ablation pattern is necessary. The surgeon may activate a "select ablation shape" mode of operation for generator assembly 28, preview an energy applicator array by reviewing graphically and textually presented data on display 21, optionally, or alternatively, manipulate a graphic image by, for example, rotating the image, and to select an array of energy applicators based upon displayed parameters. The selected energy applicator(s) may then be electrically coupled to the generator assembly 28 for use therewith.

In an embodiment, a surgeon may input via user interface 25 an applicator array parameter to cause generator assembly 28 to present one or more electromagnetic energy delivery devices corresponding thereto. For example, a surgeon may require a 3.0 cm×3.0 cm ablation pattern, and provide an input corresponding thereto. In response, the generator assembly 28 may preview a corresponding subset of available electromagnetic energy delivery devices 100 that match or correlate to the inputted parameter.

Figure 18:
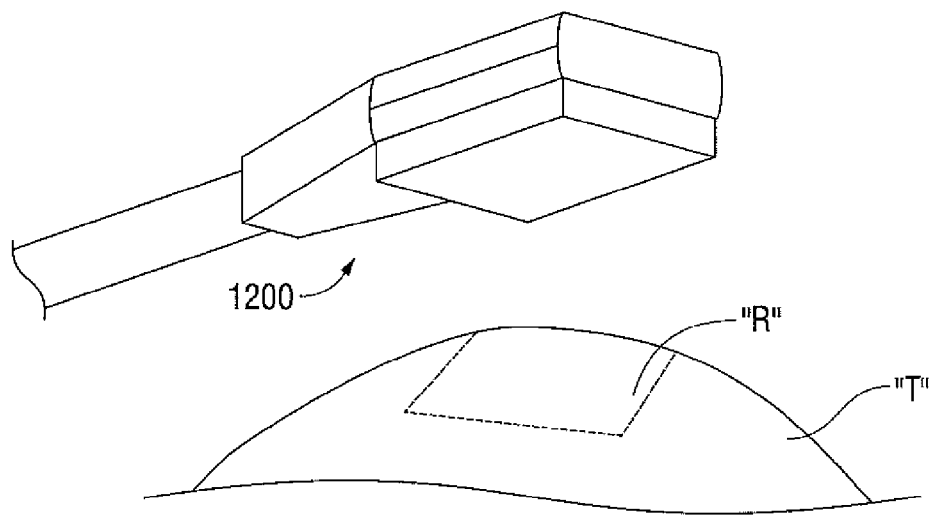
FIG. 18 is a diagrammatic representation of a radiation pattern of electromagnetic energy delivered into tissue by an electromagnetic energy delivery device, such as the electromagnetic energy delivery device of FIG. 11, according to an embodiment of the present disclosure.

FIG. 18 is a diagrammatic representation of a radiation pattern "R" of electromagnetic energy delivered into tissue "T" by an electromagnetic energy delivery device, such as the electromagnetic energy delivery device 1200 of FIG. 11, according to an embodiment of the present disclosure.

Figure 19:
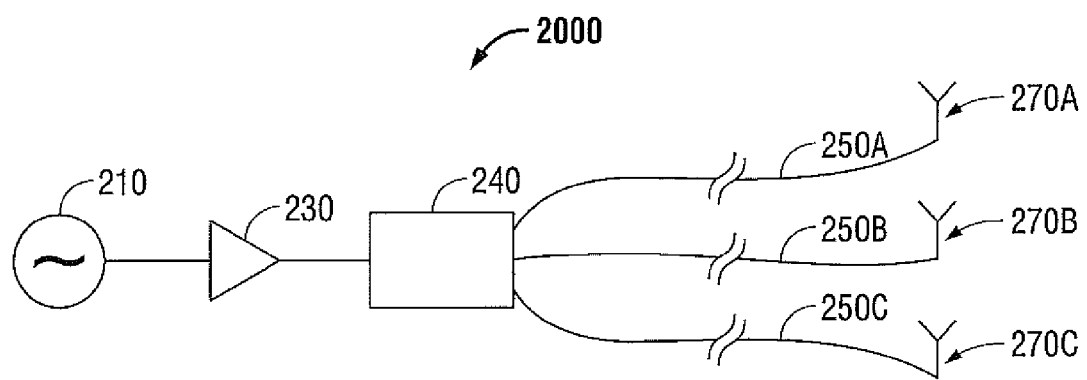
FIG. 19 is a schematic diagram of an electrosurgical system for treating tissue according to an embodiment of the present disclosure.

FIG. 19 is a schematic diagram of an electrosurgical system 2000 for treating tissue according to an embodiment of the present disclosure. Electrosurgical system 2000 includes a microwave signal source 210 providing a microwave frequency output signal to a microwave amplifier unit 230, a phase-balanced microwave power splitter 240 coupled to the microwave amplifier unit 230, and a first, a second and a third microwave ablation antenna assembly 270A, 270B and 270C, each coupled to the phase-balanced microwave power splitter 240. The microwave signal source 210 is capable of generating a plurality of output signals of various frequencies that are input to the microwave amplifier unit 230. The microwave amplifier unit 230 may have any suitable input power and output power.

In the electrosurgical system 2000, a first transmission line 250A electrically connects the first antenna assembly 270A to the phase-balanced microwave power splitter 240, defining a first channel; a second transmission line 250B electrically connects the second antenna assembly 270B to the phase-balanced microwave power splitter 240, defining a second channel; and a third transmission line 250C electrically connects the third antenna assembly 270C to the phase-balanced microwave power splitter 240, defining a third channel. The first, second and third transmission lines 250A, 250B and 250C may each include one or more electrically conductive elements, such as electrically conductive wires.

In an embodiment, the first, second and third transmission lines 250A, 250B and 250C each have substantially the same length, which preserves the phase relationship between the electrical signals in each channel of the electrosurgical system 2000. The phase-balanced microwave power splitter 240 may be implemented by any suitable power divider that provides equal power split at all output ports while substantially maintaining phase. For example, the phase-balanced microwave power splitter 240 may be implemented using a 3-way power divider that provides equal power split at all output ports while maintaining a phase balance of <+/−45 degrees. The phase-balanced microwave power splitter 240 may be implemented by any suitable power divider that provides equal power split at all output ports while substantially maintaining phase and amplitude balance. For example, in one instance, the phase-balanced microwave power splitter 240 implements using a 3-way power divider that provides equal power split at all output ports while maintaining a phase balance of <+/−10 degrees and amplitude balance of <1.5 dB.

Each antenna assembly 270A, 270B and 270C typically includes a plurality of electrodes disposed on a rigid or bendable needle or needle-like structure. The antenna assemblies 270A, 270B and 270C are positioned substantially parallel to each other, for example, spaced about 5 millimeters (mm) apart, and inserted directly into tissue or placed into the body during surgery by a clinician, or positioned in the body by other suitable methods. Although the electrosurgical system 2000 illustrated in FIG. 19 includes three microwave ablation antenna assemblies 270A, 270B and 270C, it is to be understood that any "N" number of antenna assemblies may be utilized and that phase-balanced microwave power splitter 240 may be implemented by any suitable power divider that divides or splits a microwave input signal into "N" number of output signals of equal power while substantially maintaining phase and amplitude balance.

The electrosurgical system 2000 delivers phase-controlled microwave power to each antenna assembly 270A, 270B and 270C of the three-channel system. The electrosurgical system 2000 delivers substantially in-phase microwave power to each antenna assembly 270A, 270B and 270C, which may result in a more efficient ablating tool than out-of-phase energy applicators. By controlling the phase of energy applicators with respect to each other, according to embodiments of the present disclosure, a desired effect on tissue between the energy applicators is produced. In a resection procedure where a long thin ablation line is desired, energy applicators that are 180 degrees out of phase with respect to each other produce a desired effect on tissue. In ablation procedures using in-phase energy applicators, according to various embodiments of the present disclosure, there may be a reduction in energy that might otherwise move between the antenna shafts toward the surface with out-of-phase energy applicators.

In an embodiment, the electrosurgical system 2000 delivers phase-controlled microwave power to each antenna assembly 270A, 270B and 270C while maintaining a phase balance of <+/−45 degrees. The electrosurgical system 2000 is implemented with operating frequencies in the range of about 915 MHz to about 5 GHz, which may be useful in performing ablation procedures and/or other procedures. It is to be understood that the electrosurgical system 2000 may be implemented with any appropriate range of operating frequencies.

Figure 20:
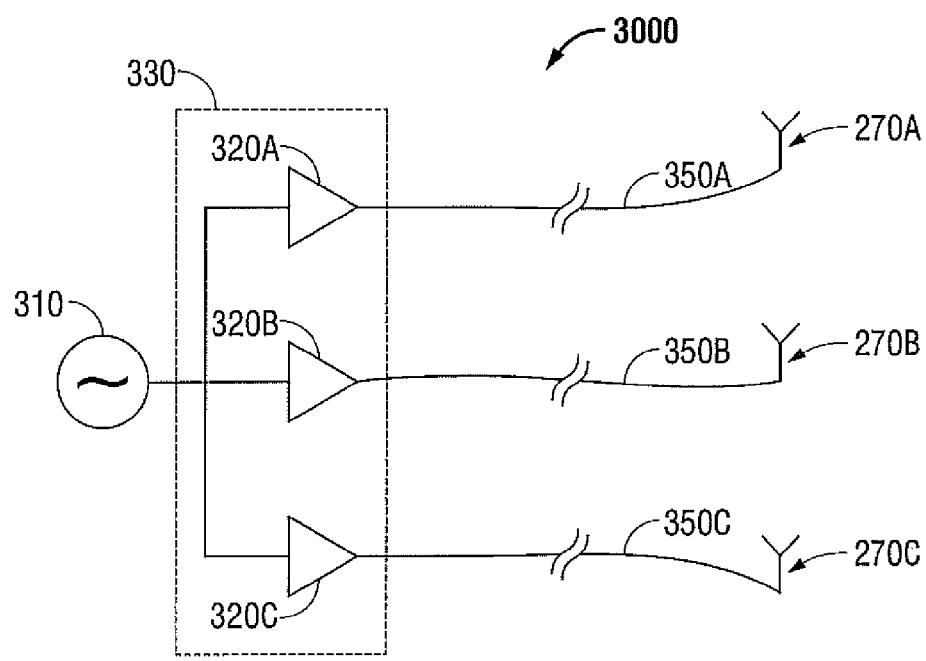
FIG. 20 is a schematic diagram of an electrosurgical system for treating tissue according to an embodiment of the present disclosure.

FIG. 20 is a schematic diagram of an embodiment of an electrosurgical system 3000 for treating tissue according to an embodiment of the present disclosure. Electrosurgical system 3000 includes a microwave signal source 310 providing a microwave frequency output signal to a controller 330, and a first, a second and a third microwave ablation antenna assembly 270A, 270B and 270C, each coupled to the controller 330. The microwave signal source 310 is capable of generating a plurality of output signals of various frequencies that are input to the controller 330.

The controller 330 includes a first, a second and a third microwave amplifier 320A, 320B and 320C that are phase-balanced with respect to one another. The first, second and third phase-balanced microwave amplifiers 320A, 320B and 320C each deliver equal power while maintaining a phase balance of <+/−10 degrees and amplitude balance of <1.5 dB. In an embodiment, the first, second and third phase-balanced microwave amplifiers 320A, 320B and 320C each deliver phase-controlled microwave power to the respective antenna assemblies 270A, 270B and 270C while maintaining a phase balance of <+/−45 degrees. The first, second and third phase-balanced microwave amplifiers 320A, 320B and 3200 may have any suitable input power and output power.

In the electrosurgical system 3000, a first transmission line 350A electrically connects the first antenna assembly 270A to the first phase-balanced microwave amplifier 320A, defining a first channel; a second transmission line 350B electrically connects the second antenna assembly 270B to the second phase-balanced microwave amplifier 320B, defining a second channel; and a third transmission line 350C electrically connects the third antenna assembly 270C to the third phase-balanced microwave amplifier 320C, defining a third channel. The first, second and third transmission lines 350A, 350B and 350C each include one or more electrically conductive elements, such as electrically conductive wires. In an embodiment, the first, second and third transmission lines 350A, 350B and 350C each have substantially the same length, which preserves the phase relationship between electrical signals in each channel of the electrosurgical system 3000.

Although the electrosurgical system 3000 illustrated in FIG. 20 includes three microwave ablation antenna assemblies 270A, 270B and 270C and three phase-balanced microwave amplifiers 320A, 3208 and 320C, it is to be understood that any "N" number of antenna assemblies and any "N" number of phase-balanced microwave amplifiers may be utilized.

Figure 21:
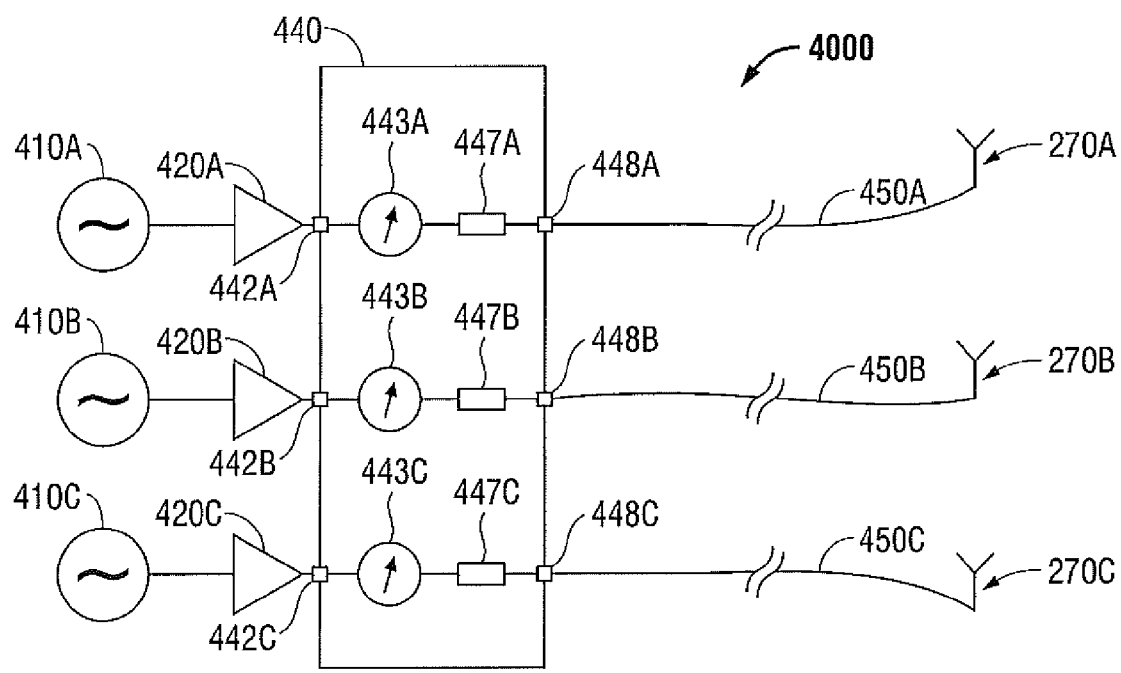
FIG. 21 is a schematic diagram of an electrosurgical system for treating tissue, according to an embodiment of the present disclosure.

FIG. 21 is a schematic diagram of an electrosurgical system 4000 for treating tissue according to another embodiment of the present disclosure. The disclosed electrosurgical system 4000 is a three-channel system that includes a first, a second and a third microwave signal source 410A, 410B and 410C, a first, a second and a third microwave amplifier 420A, 420B and 420C, a controller 440 that includes three inputs 442A, 442B and 442C and three outputs 448A, 448B and 448C, and a first, a second and a third microwave ablation antenna assembly 270A, 270B and 270C.

The first, second and third microwave signal sources 410A, 410B and 410C provide microwave frequency output signals to the first, second and third amplifiers 420A, 420B and 420C, respectively. The first microwave amplifier 420A provides an output signal through an output terminal that is electrically coupled to the first input 442A of the controller 440; the second microwave amplifier 420B provides an output signal through an output terminal that is electrically coupled to the second input 442B of the controller 440; and the third microwave amplifier 420C provides an output signal through an output terminal that is electrically coupled to the third input 442C of the controller 440. The first, second and third amplifiers 420A, 420B and 420C each have any suitable input power and output power. In an embodiment, the first, second and third amplifiers 420A, 420B and 420C may be phase-balanced with respect to one another and, in such case, are arranged between the controller 440 and the first, second and third microwave ablation antenna assemblies 270A, 270B and 270C.

Although the first, second and third amplifiers 420A, 420B and 420C are illustrated as standalone modules in FIG. 21, it is to be understood that one or more of the amplifiers may be integrated fully or partially into the controller 440. The electrosurgical system 4000 may be implemented without the first, second and third amplifiers 420A, 420B and 420C, or with any combination thereof.

The controller 440 includes a first, a second and a third phase shifter 443A, 443B and 443C, and a first, a second and a third phase monitor unit 447A, 447B and 447C. The first phase shifter 443A is electrically coupled between the first input 442A and the first phase monitor unit 447A; the second phase shifter 443B is electrically coupled between the second input 442B and the second phase monitor unit 447B; and the third phase shifter 443C is electrically coupled between the third input 442C and the third phase monitor unit 447C. The first phase monitor unit 447A is electrically coupled between the first phase shifter 443A and the output 448A; the second phase monitor unit 447B is electrically coupled between the second phase shifter 443B and the output 448B; and the third phase monitor unit 447C is electrically coupled between the third phase shifter 443C and the output 448C.

The controller 440 may include a number of processing units (not shown) coupled to the first, second and third phase monitor units 447A, 447B and 447C for controlling output of one or more of the phase shifters 443A, 443B and 443C to provide a desired phase relationship of electrical signals in each channel of the electrosurgical system 4000. The processing unit(s) may include multiple processors and/or multicore CPUs and may include any type of processor capable of executing software, such as a microprocessor, digital signal processor, microcontroller, or the like. The controller 440 may additionally, or alternatively, be operably coupled to an external processor (e.g., 82 shown in FIG. 16).

The controller 440 may include one or more phase detectors (not shown) to compare the respective phases of electrical signals inputted through the inputs 442A, 442B and/or 442C. By comparing a reference signal, such as a clock signal, to a feedback signal using a phase detector, phase adjustments may be made based on the comparison of the electrical signals inputted, to set the phase relationship between electrical signals in each channel of the electrosurgical system 4000.

In an embodiment, the controller 440 delivers phase-controlled microwave power through the outputs 448A, 448B and 448C to the antenna assemblies 270A, 270B and 270C, respectively irrespective of the individual phases of each of electrical signals inputted through the inputs 442A, 442B and/or 442C. As illustrated in FIG. 21, a first transmission line 450A electrically connects the first antenna assembly 270A to the output 448A of the controller 440, defining a first channel; a second transmission line 450B electrically connects the second antenna assembly 270B to the output 448B of the controller 440, defining a second channel; and a third transmission line 450C electrically connects the third antenna assembly 270C to the output 448C of the controller 440, defining a third channel. The first, second and third transmission lines 450A, 450B and 450C each include one or more electrically conductive elements, such as electrically conductive wires. In an embodiment, the first, second and third transmission lines 450A, 450B and 450C each have substantially the same length, which preserves the phase relationship between electrical signals in each channel of the electrosurgical system 4000.

Hereinafter, a method of manufacturing an energy applicator having a dielectric loaded coaxial aperture with distally positioned resonant structure, in accordance with the present disclosure, is described with reference to FIG. 22. It is to be understood that the steps of the method provided herein may be performed in combination and in a different order than presented herein without departing from the scope of the disclosure.

Figure 22:
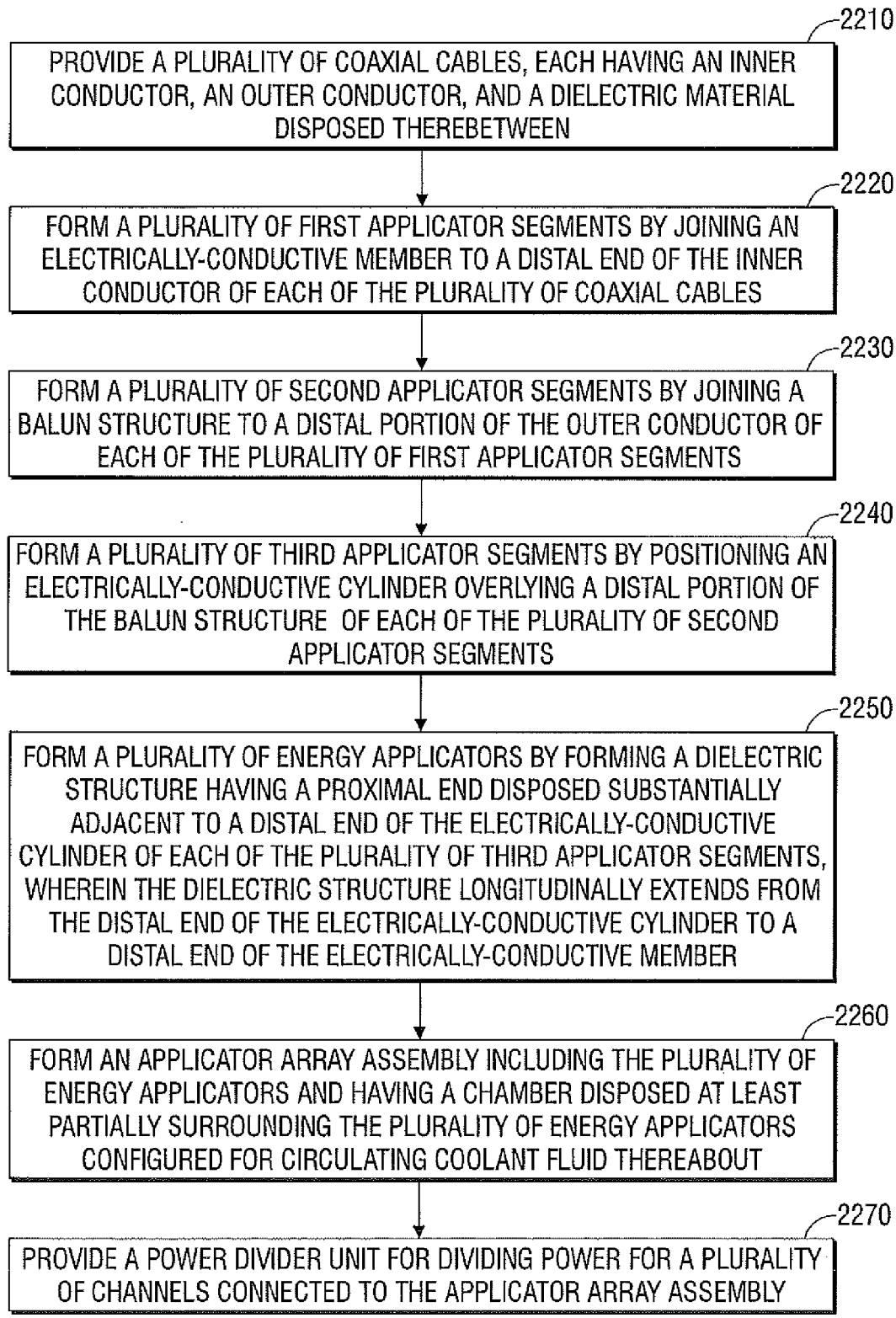
FIG. 22 is a flowchart illustrating a method of manufacturing an electromagnetic energy delivery device according to an embodiment of the present disclosure.

FIG. 22 is a flowchart illustrating a method of manufacturing an electromagnetic energy delivery device according to an embodiment of the present disclosure. In step 2210, a plurality of coaxial cables is provided. Each coaxial cable (e.g., 226 shown in FIG. 2) includes an inner conductor (e.g., 220 shown in FIG. 2), an outer conductor (e.g., 224 shown in FIG. 2) and a dielectric material (e.g., 222 shown in FIG. 2) disposed therebetween, A portion of the inner conductor and the dielectric material (e.g., 221 shown in FIG. 2) may extend beyond the outer conductor at the distal end of the coaxial cable.

In step 2220, a plurality of first applicator segments is formed by joining an elongated electrically-conductive member (e.g., 260 shown in FIG. 2) to the distal end of the inner conductor (e.g., 220 shown in FIG. 2) of each of the plurality of coaxial cables. In some embodiments, the electrically-conductive member is a solid metal cylinder electrically coupled to the inner conductor, e.g., by solder or other suitable electrical connection.

In step 2230, a plurality of second applicator segments is formed by joining a balun structure (e.g., "B" shown in FIG. 4) to a distal portion of the outer conductor (e.g., 224 shown in FIG. 3) of each of the plurality of first applicator segments.

The balun structure may be a quarter wavelength sleeve balun. In some embodiments, the balun structure includes a balun insulator (e.g., 322 shown in FIG. 3) coaxially disposed around a distal portion of the outer conductor, and an electrically-conductive balun sleeve (e.g., 430 shown in FIG. 4) coaxially disposed around a proximal portion of the balun insulator, wherein the conductive balun sleeve is electrically coupled to the outer conductor. The balun insulator may extend distally beyond the distal end of the electrically-conductive balun sleeve to direct currents into the balun.

In step 2240, a plurality of third applicator segments is formed by positioning an electrically-conductive cylinder (e.g., 540 shown in FIG. 5) overlying a distal portion of the balun structure of each of the plurality of second applicator segments. In some embodiments, a portion (e.g., 642 shown in FIG. 7) of the electrically-conductive cylinder (e.g., 640 shown in FIGS. 6 and 7) extends distally beyond the distal edge of an electrically-conductive balun sleeve (e.g., 630 shown in FIG. 7) of the balun. In some embodiments, the electrically-conductive cylinder is positioned relative to the distal edge of the electrically-conductive balun sleeve such that the combined length of the conductive balun sleeve and the conductive cylinder is a quarter wavelength or a half wavelength.

In step 2250, a plurality of energy applicators is formed by forming a dielectric structure (e.g., 850 shown in FIG. 8) having a proximal end disposed substantially adjacent to a distal end of the electrically-conductive cylinder of each of the plurality of third applicator segments, wherein each dielectric structure longitudinally extends from the distal end of the electrically-conductive cylinder to a distal end of the electrically-conductive member. In some embodiments, the dielectric structure includes a cap of dielectric material (e.g., 852 shown in FIG. 8) configured to cover the distal end of the electrically-conductive member. The dielectric structure may be formed using over-molding techniques or other forming techniques.

In step 2260, an applicator array assembly (e.g., 950 shown in FIG. 9) is formed including the plurality of energy applicators (e.g., 811, 812, 813 shown in FIG. 9) and a cooling chamber (e.g., 1060 shown in FIG. 10) disposed at least partially surrounding the plurality of energy applicators configured for circulating coolant fluid (e.g., "F" shown in FIG. 11) thereabout.

In step 2270, a power divider unit (e.g., 940 shown in FIG. 11) for dividing power for a plurality of channels (e.g., 250A, 250B, 250C shown in FIG. 19) connected to the applicator array assembly is provided, wherein each channel may be connectable to any one or more of the energy applicators of the applicator array assembly.

The above-described electrosurgical systems for treating tissue and methods of directing electromagnetic radiation to a target volume of tissue may be used to provide directional microwave ablation, wherein the heating zone may be focused to one side of the electrosurgical device, thereby allowing clinicians to target small and/or hard tumors without having to penetrate the tumor directly or kill more healthy tissue than necessary. The presently disclosed electrosurgical devices may allow clinicians to avoid ablating critical structures, such as large vessels, healthy organs or vital membrane barriers, by placing the electrosurgical device between the tumor and critical structure and directing the electromagnetic radiation toward the tumor and away from the sensitive structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical system for directing energy to tissue, comprising:
   a generator assembly operable to supply power having a selected phase, amplitude and frequency; and
   an applicator array assembly including:
   a shell assembly;
   a plurality of energy applicators disposed within the shell assembly, each one of the plurality of energy applicators including:
      a length of coaxial cable having an inner conductor, an outer conductor coaxially disposed around the inner conductor, and a dielectric material disposed therebetween;
      an elongated electrically-conductive member longitudinally disposed at a distal end of the inner conductor;
      a balun structure disposed on the outer conductor;
      an electrically-conductive cylinder coaxially disposed around a distal portion of the balun structure; and
      a dielectric structure disposed substantially adjacent to a distal end of the electrically-conductive cylinder, wherein the dielectric structure longitudinally extends from the distal end of the electrically-conductive cylinder to a distal end of the electrically-conductive member; and
   a power divider unit electrically coupled to the generator assembly, the power divider unit operable to divide power into the applicator array assembly.

2. The electrosurgical system of claim 1, wherein the power divider unit includes a plurality of phase shifters.

3. The electrosurgical system of claim 2, wherein the power divider unit further includes a plurality of phase monitor units electrically coupled between the plurality of phase shifters and the plurality of energy applicators.

4. The electrosurgical system of claim 1, wherein the power divider unit includes a phase-balanced microwave power splitter.

5. The electrosurgical system of claim 4, wherein the power divider unit provides a substantially equal power split to the plurality of energy applicators while maintaining a phase balance of <+/−45 degrees.

6. The electrosurgical system of claim 1, wherein the shell assembly includes an outer portion formed of an electrically-conductive material.

7. The electrosurgical system of claim 1, wherein the shell assembly has a substantially rectangular shape.

8. The electrosurgical system of claim 1, wherein the generator assembly includes:
   a generator module configured to provide electromagnetic energy;
   a processor operably coupled to the generator module; and
   a user interface operably coupled to the processor, wherein the user interface is configured to display an image corresponding to ablation pattern associated with an applicator array assembly.

9. The electrosurgical system of claim 8, wherein the generator assembly further includes:
   a database in operable communication with the processor and adapted to store parameters associated with at least one applicator array assembly.

10. The electrosurgical system of claim 1, wherein the balun structure is a quarter wavelength sleeve.

11. The electrosurgical system of claim 1, wherein the shell assembly includes an outer portion formed of an electrically-conductive material, the outer portion electrically coupled to the distal end of the conductive balun sleeve of at least one of the plurality of energy applicators.

* * * * *